(12) United States Patent
Staehle et al.

(10) Patent No.: US 9,029,387 B2
(45) Date of Patent: May 12, 2015

(54) BENZONAPHTHYRIDINAMINES AS AUTOTAXIN INHIBITORS

(75) Inventors: Wolfgang Staehle, Ingelheim (DE); Melanie Schultz, Darmstadt (DE); Kai Schiemann, Seeheim-Jugenheim (DE)

(73) Assignee: Merck Patent GmbH, Darmstadt (DE)

( * ) Notice: Subject to any disclaimer, the term of this patent is extended or adjusted under 35 U.S.C. 154(b) by 191 days.

(21) Appl. No.: 13/637,161

(22) PCT Filed: Feb. 28, 2011

(86) PCT No.: PCT/EP2011/000964
§ 371 (c)(1),
(2), (4) Date: Sep. 25, 2012

(87) PCT Pub. No.: WO2011/116867
PCT Pub. Date: Sep. 29, 2011

(65) Prior Publication Data
US 2013/0012505 A1    Jan. 10, 2013

(30) Foreign Application Priority Data

Mar. 26, 2010 (EP) ..................................... 10003282

(51) Int. Cl.
| | |
|---|---|
| A01N 43/42 | (2006.01) |
| A61K 31/44 | (2006.01) |
| A61K 31/497 | (2006.01) |
| A61K 31/535 | (2006.01) |
| C07D 471/00 | (2006.01) |
| C07D 491/00 | (2006.01) |
| C07D 498/00 | (2006.01) |
| C07D 513/00 | (2006.01) |
| C07D 515/00 | (2006.01) |
| C07D 401/00 | (2006.01) |
| C07D 413/00 | (2006.01) |
| C07D 471/04 | (2006.01) |

(52) U.S. Cl.
CPC ................................... C07D 471/04 (2013.01)

(58) Field of Classification Search
USPC .................. 514/292, 253.03, 232.08; 546/81; 544/361, 236
See application file for complete search history.

(56) References Cited

U.S. PATENT DOCUMENTS

| 4,985,430 A | 1/1991 | Morita et al. |
| 6,294,547 B1 | 9/2001 | Oka et al. |

FOREIGN PATENT DOCUMENTS

| EP | 0 997 462 A1 | 5/2000 |
| GB | 1 186 061 A | 4/1970 |
| JP | 1-250353 | 5/1989 |

OTHER PUBLICATIONS

International Search Report of PCT/EP2011/000964 (May 16, 2011).
A.B. Hoeglund et al., "Characterization of Non-Lipid Autotaxin Inhibitors", Bioorganic & Medicinal Chemistry, vol. 18, No. 2 (2010) pp. 769-776.
F. Gatta et al., "Synthesis of 10-Amino-1,2,3,4-Tetrahydrobenzo[b][1,6]-Naphthyridines and Related Derivatives", Journal of Heterocyclic Chemistry, vol. 33 (1996) pp. 1807-1813.
Office Action for JP-2013-500359; dated Feb. 3, 2015.
Mitsubishi Kasei Corp; "9-Acylamino-Tetrahydroacrydine Derivative And Dysmnesia Improver Containing The Compound As An Active Ingredient" Patent Abstracts of Japan; May 10, 1989; English Abstract of JP 01-250353.

*Primary Examiner* — Samira Jean-Louis
(74) *Attorney, Agent, or Firm* — Millen, White, Zelano & Branigan, P.C.

(57) ABSTRACT

The present invention relates to benzonaphthyridinamines of the formula (I) as autotaxin inhibitors and to the use thereof in the treatment and/or prophylaxis of physiological and/or pathophysiological conditions in which the inhibition, regulation and/or modulation of phosphodiesterase or lysophospholipase autotaxin plays a role, in particular of various types of cancer and autoimmune and inflammatory diseases.

11 Claims, No Drawings

BENZONAPHTHYRIDINAMINES AS AUTOTAXIN INHIBITORS

TECHNICAL AREA

The present invention relates to benzonaphthyridinamines as autotaxin inhibitors and to the use thereof in the treatment and/or prophylaxis of physiological and/or pathophysiological conditions in which the inhibition, regulation and/or modulation of phosphodiesterase or lysophospholipase autotaxin plays a role, in particular of various types of cancer and autoimmune and inflammatory diseases.

PRIOR ART

Autotaxin (ATX) is an enzyme which is responsible for the increase in the lysophosphatidic acid level in ascites and plasma (Xu et al., Clinical Cancer Research 1995, 1: 1223 and Xu et al., Biochem. J. 1995, 309: 933). ATX converts lysophatidylcholine (LPC) into lysophosphatidic acid (Tokumura et al., J. Biol. Chem. 2002, 277: 39436 and Umezu-Gozo et al., J. Biol. Chem. 2002, 158: 227).

LPA is an intercellular lipid mediator which influences a multiplicity of biological and biochemical processes, such as, for example, smooth muscle contraction, thrombocyte aggregation and apoptosis (Tigyi et al., Prog. Lipid Res 2003, 42: 498 and Mills et al., Nat. Rev. Cancer 2003, 3: 582 and Lynch et al., Prost. Lipid Med 2001, 64: 33). In addition, LPA can be found in increased concentrations in plasma and ascites fluid from ovarian cancer patients in the early and late phase. LPA plays a role there in tumour cell proliferation and invasion thereof into neighbouring tissue, which can result in metastasisation (Xu et al., Clinical Cancer Research 1995, 1: 1223 and Xu et al., Biochem. J. Vol. 1995, 309: 933). These biological and pathobiological processes are switched on by the activation by LPA of G-protein-coupled receptors (Contos et al., Mol. Pharm. 2000, 58: 1188). For this reason, it is desirable to lower the LPA level for the treatment of tumour patients. This can be achieved by the inhibition of enzymes which are involved in LPA biosynthesis, such as, for example, autotaxin (ATX, Sano et al., J. Biol. Chem. 2002, 277: 21197 and Aoki et al., J. Biol. Chem. 2003, 277: 48737).

Autotaxin belongs to the enzyme family of the nucleotides pyrophosphatases and phosphodiesterases (Goding et al., Immunol. Rev. 1998, 161: 11) and represents an important starting point in antitumour therapy (Mills et al., Nat. Rev. Cancer 2003, 3: 582 and Goto et al., J. Cell. Biochem. 2004, 92: 1115), since it is expressed to an increased extent in tumours and causes tumour cell proliferation and invasion into neighbouring tissue, which can result in metastases formation (Nam et al., Oncogene 2000, 19: 241). In addition, autotaxin together with other angiogenetic factors causes blood vessel formation in the course of angiogenesis (Nam et al., Cancer Res. 2001, 61: 6938). Angiogenesis is an important process in tumour growth, which ensures supply of the tumour with nutrients. For this reason, inhibition of angiogenesis is an important starting point in cancer and tumour therapy, with which the tumour can be starved to a certain extent (Folkman, Nature Reviews Drug Discovery 2007, 6: 273-286).

Compounds which are capable of inhibiting autotaxin are described in Peng et al. (Bioorganic & Medicinal Chemistry Letters 2007, 17: 1634-1640). The compounds described therein are lipid analogues, which do not have any structural features in common with the compounds according to the invention.

Further prior-art documents are as follows:

U.S. Pat. No. 3,637,706, U.S. Pat. No. 3,647,800 and U.S. Pat. No. 3,674,790 describe benzonaphthyridine derivatives which differ from the compounds according to the invention in their substitution in position 2.

Yamato M et al. (Journal of Medicinal Chemistry 1989, 32(6): 1295-1300) describe benzonaphthyridine derivatives which differ from the compounds according to the invention in their substitution in position 2.

U.S. Pat. No. 4,751,305 and U.S. Pat. No. 4,808,612 describe benzonaphthyridine derivatives which differ from the compounds according to the invention in their substitution in position 2.

U.S. Pat. No. 4,816,464 describes specific benzonaphthyridine derivatives which differ from the compounds according to the invention in their substitution in position 2.

Yamato M et al. (Chemical & Pharmaceutical Bulletin 1990, 38(11): 3048-3052 describe benzonaphthyridine derivatives which differ from the compounds according to the invention in their substitution in position 2.

JP 3-218359 describes benzonaphthyridine derivatives which differ from the compounds according to the invention in their substitution in position 2.

Skotnicki J S et al. (Medicinal Chemistry Research 1991, 1(4): 254-252) describe hydrazine benzonaphthyridine derivatives which differ from the compounds according to the invention in their substitution in position 10.

Pirrung M C et al. (Chemistry & Biology 1995, 2 (9): 621-626) describe a benzonaphthyridine derivative which differs from the compounds according to the invention in position 2.

Youssef, Khairia M et al. (Bulletin of the Faculty of Pharmacy (Cairo University) 1995, 33(1): 33-39) and Youssef, Khairia M (Al-Azhar Bulletin of Science 1999, 10(1): 99-112) describe hydrazine benzonaphthyridine derivatives which differ from the compounds according to the invention in their substitution in position 10.

Novel naphthyridine derivatives having an antagonistic effect on tachykinin receptors are described in WO 99/00388, which differ from the compounds according to the invention in their substitution in position 10.

WO 2000/035918 describes, inter alia, benzonaphthyridine derivatives as tachykinin receptor antagonists which differ from the compounds according to the invention in their substitution in position 2.

JP 2002-088081 describes, inter alia, benzonaphthyridine derivatives as tachykinin antagonists which differ from the compounds according to the invention in their substitution in position 2.

WO 2004/067513 describes, inter alia, a benzonaphthyridine derivative (Example 25), but this differs from the compounds according to the invention in position 2.

International application PCT/EP2009/007930, filed on Nov. 11, 2009, describes benzonaphthyridine derivatives which differ from the compounds according to the invention in their substitution in position 10.

The incorporation of a citation into this application does not state that the citation represents relevant prior art for this application.

DESCRIPTION OF THE INVENTION

The object of the present invention is the provision of novel autotaxin inhibitors.

The object of the present invention has surprisingly been achieved in one aspect by provision of compounds of the formula (I)

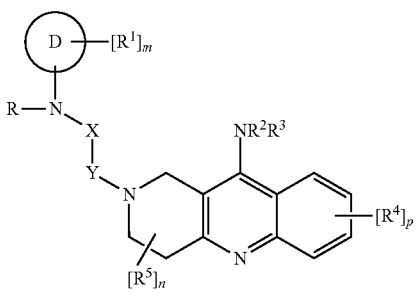

in which:

D denotes Ar or Het,

Ar denotes unsubstituted or mono- or polysubstituted phenyl, indanyl, naphthyl or biphenyl, where, however, unsubstituted phenyl is optionally and preferably excluded, Het denotes a mono- or bicyclic saturated, partially unsaturated or aromatic heterocycle having 1, 2, 3 or 4 N, O and/or S atoms, which may be unsubstituted or mono- or polysubstituted, X, Y each, independently of one another, is absent, denote —CH$_2$—, —(CH$_2$)$_2$—, —C(O)—, —CHOH— or —CH$_2$OC(O)—, where only one of the radicals X or Y may be absent, R in each case, independently of one another, denote H, A, Cyc, (CH$_2$)$_q$Ar or (CH$_2$)$_q$Het and may be mono- or polysubstituted by R$^6$, where in A and Cyc, the C chain and C ring respectively may also be interrupted by O, R$^1$ in each case, independently of one another, denote R, F, Cl, Br, I, OH, =O, CN, NO$_2$, NRR, NHC(O)R, NHSO$_2$R, OR, C(O)R, C(O)NRR, CF$_3$, OCF$_3$, SCF$_3$, SO$_2$CH$_3$, SO$_3$R, SO$_2$R, SO$_2$NR, SR, OA, A, phenyl and may be mono- or polysubstituted by R$^6$, R$^2$, R$^3$ each, independently of one another, denote R, where R$^2$ and R$^3$ may alternatively together also form Cyc or Het, each of which may in turn be mono- or polysubstituted by R$^6$, R$^4$ in each case, independently of one another, denote R, F, Cl, Br, I, OH, =O, CN, NO$_2$, NRR, NHC(O)R, NHSO$_2$R, OR, C(O)R, C(O)NRR, CF$_3$, OCF$_3$, SCF$_3$, SO$_2$CH$_3$, SO$_3$R, SO$_2$R, SO$_2$NR, SR, OA, A, phenyl and may be mono- or polysubstituted by R$^6$, R$^5$ in each case, independently of one another, denote R, F, Cl, Br, I, OH, =O, CN, NO$_2$, NRR, NHC(O)R, NHSO$_2$R, OR, C(O)R, C(O)NRR, CF$_3$, OCF$_3$, SCF$_3$, SO$_2$CH$_3$, SO$_3$R, SO$_2$R, SO$_2$NR, SR, OA, A, phenyl and may be mono- or polysubstituted by R$^6$, R$^6$ in each case, independently of one another, denote R, F, Cl, Br, I, OH, =O, CN, NO$_2$, NRR, NHC(O)R, NHSO$_2$R, OR, C(O)R, C(O)NRR, CF$_3$, OCF$_3$, SCF$_3$, SO$_2$CH$_3$, SO$_3$R, SO$_2$R, SO$_2$NR, SR, OA, A, phenyl and, so long as a substitution is chemically possible, may be mono- or polysubstituted by R, F, Cl, Br, I, OH, =O, CN, NO$_2$, NRR, NHC(O)R, NHSO$_2$R, OR, C(O)R, C(O)NRR, CF$_3$, OCF$_3$, SCF$_3$, SO$_2$CH$_3$, SO$_3$R, SO$_2$R, SO$_2$NR, SR, OA, A, phenyl, A denotes linear or branched alkyl having 1, 2, 3, 4, 5, 6, 7 or 8 C atoms, in which 1, 2, 3, 4, 5, 6 or 7H atoms may be replaced by OR, CN, NRR, F and/or Cl and/or in which one or two non-adjacent CH$_2$ groups may be replaced by O, NH, S, SO, SO$_2$ and/or by CH=CH groups, Cyc denotes cyclic alkyl having 3, 4, 5, 6, 7, 8, 9, 10, 11, 12, 13 or 14 C atoms, m denotes 0, 1, 2, 3, 4, or 5, n denotes 0, 1, 2, or 3, p denotes 0, 1, 2, 3, or 4, q denotes 0, 1, or 2, and pharmaceutically usable salts, solvates and stereoisomers thereof, including mixtures thereof in all ratios.

The invention furthermore relates to preferred, in each case independent embodiments of compounds of the formula (I) as defined here, in each of which, independently of one another:

Preferred embodiment (A):
D denotes Ar,

Preferred embodiment (B):
Ar denotes unsubstituted or mono- or polysubstituted phenyl, but preferably denotes mono- or polysubstituted phenyl, Preferred embodiment (C):
X, Y each, independently of one another, denote —CH$_2$—, —C(O)— or —CH$_2$OC(O)—, X is preferably =C(O)— and Y is preferably =—CH$_2$— or —CH$_2$OC(O)—, Preferred embodiment (D):
R$^1$ in each case, independently of one another, denote F, Cl, OA or OCH$_3$, Preferred embodiment (E):
R$^2$, R$^3$ each, independently of one another, denote H, Ar, Ar mono-substituted by OA, Het, Het monosubstituted by A, CH$_2$-Het, A, A monosubstituted by OH or by NRR or by CO—NRR or by Het or by CO—R, or each, independently of one another, denote 1-methylpiperidin-4-yl, 2-hydroxyethyl, 2-dimethylaminoethyl, methylcarbamoylmethyl, dimethylcarbamoylmethyl, 1H-benzimidazol-2-ylmethyl, 2-oxo-2-pyrrolidin-1-ylethyl, 2-oxo-2-piperidin-1-ylethyl, 2-morpholin-4-yl-2-oxoethyl, cyclohexylcarbamoylmethyl, 2-(4-methylpiperazin-1-yl)-2-oxoethyl, 2-(4-isopropylpiperazin-1-yl)-2-oxoethyl, diethylcarbamoylmethyl, 2-(4-benzylpiperazin-1-yl)-2-oxoethyl, 3-oxo-3-piperidin-1-ylpropyl, pyridin-4-yl, pyridin-3-yl, phenyl, pyridin-2-yl or 4-methoxyphenyl, where R$^2$ and R$^3$ may alternatively together also form 4-(2-hydroxyethyl)piperazin-1-yl, Preferred embodiment (F):
m denotes 2, Preferred embodiment (G):
n denotes 0, Preferred embodiment (H):
p denotes 0, Preferred embodiment (I):
q denotes 0 or 1, and pharmaceutically usable salts, solvates and stereoisomers thereof, including mixtures thereof in all ratios.

In a preferred embodiment, the invention furthermore relates to compounds of the formula (I) as defined here and preferred embodiments depicted here, in each of which, independently of one another:

D denotes Ar,

Ar denotes unsubstituted or mono- or polysubstituted phenyl, but preferably denotes mono- or polysubstituted phenyl, X, Y each, independently of one another, denote —CH$_2$—, —C(O)— or —CH$_2$OC(O)—, X is preferably =C(O)— and Y is preferably =—CH$_2$— or —CH$_2$OC(O)—, R$^1$ in each case, independently of one another, denote F, Cl, OA or OCH$_3$, R², R³ each, independently of one another, denote H, Ar, Ar mono-substituted by OA, Het, Het monosubstituted by A, CH₂-Het, A, A monosubstituted by OH or by NRR or by CO—NRR or by Het or by CO—R, or each, independently of one another, denote 1-methylpiperidin-4-yl, 2-hydroxyethyl, 2-dimethylaminoethyl, methylcarbamoylmethyl, dimethylcarbamoylmethyl, 1H-benzimidazol-2-ylmethyl, 2-oxo-2-pyrrolidin-1-ylethyl, 2-oxo-2-piperidin-1-ylethyl, 2-morpholin-4-yl-2-oxoethyl, cyclohexylcarbamoylmethyl, 2-(4-methylpiperazin-1-yl)-2-oxoethyl, 2-(4-isopropylpiperazin-1-yl)-2-oxoethyl, diethylcarbamoylmethyl, 2-(4-benzylpiperazin-1-yl)-2-oxoethyl, 3-oxo-3-piperidin-1-ylpropyl, pyridin-4-yl, pyridin-3-yl, phenyl, pyridin-2-yl or 4-methoxyphenyl, where R² and R³ may alternatively together also form 4-(2-hydroxyethyl)piperazin-1-yl, m denotes 2,
n denotes 0,
p denotes 0,
q denotes 0 or 1, Het, R, R⁶, A and Cyc have the indicated meanings defined here, and pharmaceutically usable salts, solvates and stereoisomers thereof, including mixtures thereof in all ratios.

In a further aspect, the object of the invention has surprisingly been achieved by provision of a compound selected from the group consisting of:

| Compound No. | Chemical Structure | Chemical Name |
|---|---|---|
| 1 | 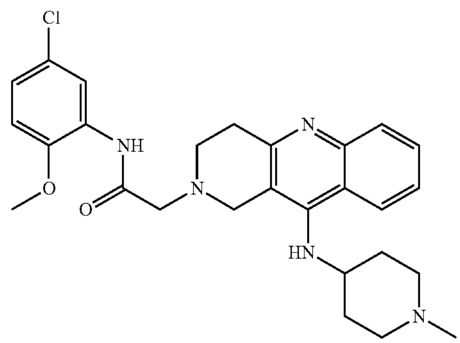 [SMILES: COc1ccc(Cl)cc1NC(=O)CN1CCc2nc3ccccc3c(NC3CCN(C)CC3)c2C1] | N-(5-Chloro-2-methoxyphenyl)-2-[10-(1-methyl-piperidin-4-ylamino)-3,4-dihydro-1H-benzo[b]-1,6-naphthyridin-2-yl]-acetamide |
| 2 | 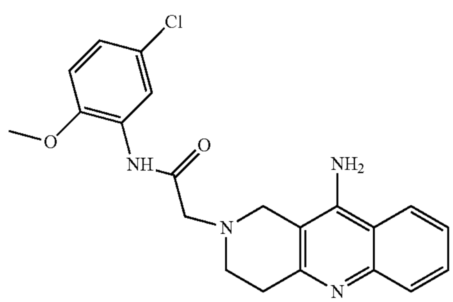 [SMILES: COc1ccc(Cl)cc1NC(=O)CN1CCc2nc3ccccc3c(N)c2C1] | 2-(10-Amino-3,4-dihydro-1H-benzo[b]-1,6-naphthyridin-2-yl)-N-(5-chloro-2-methoxyphenyl)-acetamide |
| 3 | 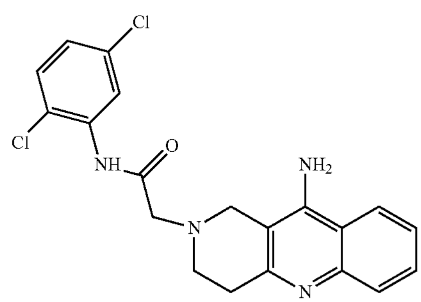 [SMILES: Nc1c2c(nc3ccccc13)CCN(CC(=O)Nc1cc(Cl)ccc1Cl)C2] | 2-(10-Amino-3,4-dihydro-1H-benzo[b]-1,6-naphthyridin-2-yl)-N-(2,5-dichlorophenyl)acetamide |
| 4 | 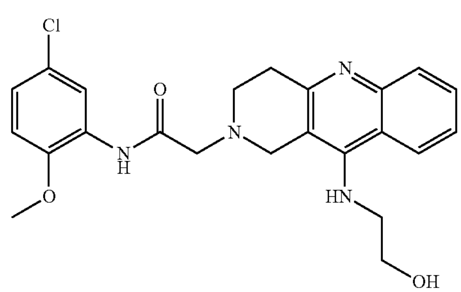 [SMILES: COc1ccc(Cl)cc1NC(=O)CN1CCc2nc3ccccc3c(NCCO)c2C1] | N-(5-Chloro-2-methoxyphenyl)-2-[10-(2-hydroxy-ethylamino)-3,4-dihydro-1H-benzo[b]-1,6-naphthyridin-2-yl]-acetamide |

| Compound No. | Chemical Structure | Chemical Name |
|---|---|---|
| 5 | 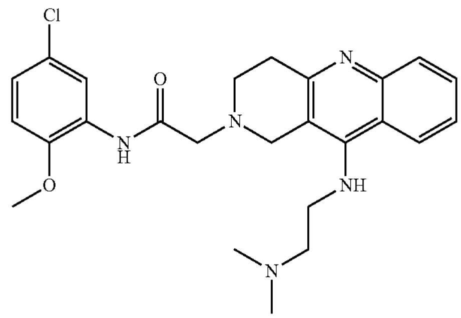 [SMILES: COc1ccc(Cl)cc1NC(=O)CN1CCc2nc3ccccc3c(NCCN(C)C)c2C1] | N-(5-Chloro-2-methoxyphenyl)-2-[10-(2-dimethylamino-ethylamino)-3,4-dihydro-1H-benzo[b]-1,6-naphthyridin-2-yl]-acetamide |
| 6 | 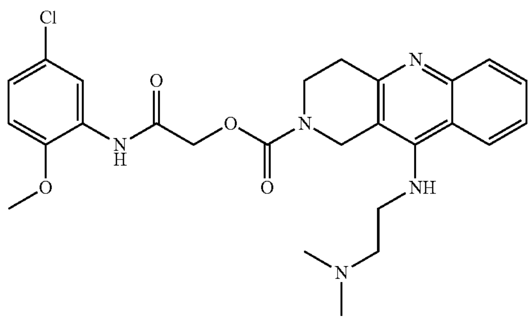 [SMILES: COc1ccc(Cl)cc1NC(=O)COC(=O)N1CCc2nc3ccccc3c(NCCN(C)C)c2C1] | 10-(2-Dimethylamino-ethylamino)-3,4-dihydro-1H-benzo[b]-1,6-naphthyridine-2-carboxylic acid (5-chloro-2-methoxy-phenylcarbamoyl)-methyl ester |
| 7 | 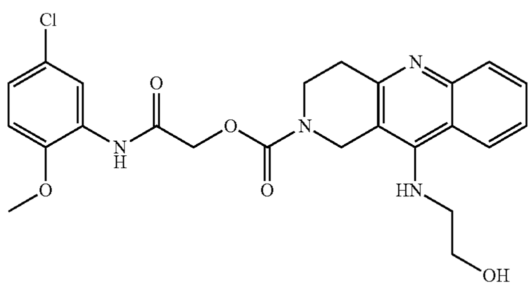 [SMILES: COc1ccc(Cl)cc1NC(=O)COC(=O)N1CCc2nc3ccccc3c(NCCO)c2C1] | 10-(2-Hydroxy-ethylamino)-3,4-dihydro-1H-benzo[b]-1,6-naphthyridine-2-carboxylic acid (5-chloro-2-methoxy-phenylcarbamoyl)-methyl ester |
| 8 | 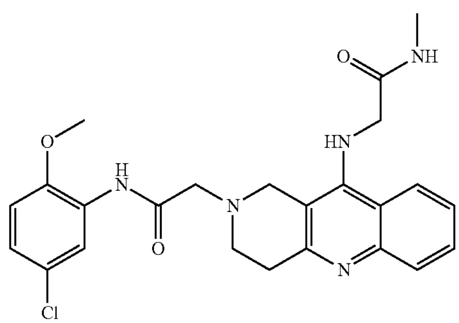 [SMILES: CNC(=O)CNc1c2c(nc3ccccc13)CCN(CC(=O)Nc1cc(Cl)ccc1OC)C2] | N-(5-Chloro-2-methoxyphenyl)-2-[10-(methylcarbamoyl-methylamino)-3,4-dihydro-1H-benzo[b]-1,6-naphthyridin-2-yl]-acetamide |
| 9 | 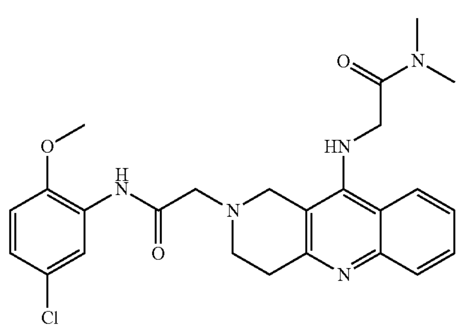 [SMILES: COc1ccc(Cl)cc1NC(=O)CN1CCc2nc3ccccc3c(NCC(=O)N(C)C)c2C1] | N-(5-Chloro-2-methoxyphenyl)-2-[10-(dimethylcarbamoyl-methylamino)-3,4-dihydro-1H-benzo[b]-1,6-naphthyridin-2-yl]-acetamide |

-continued

| Compound No. | Chemical Structure | Chemical Name |
|---|---|---|
| 10 | 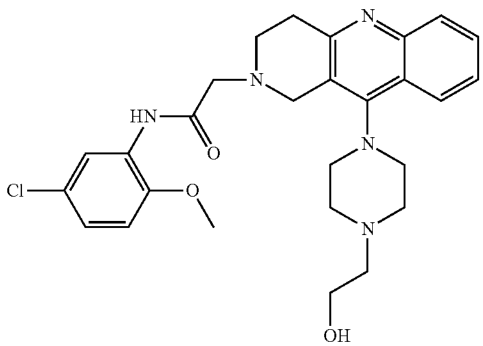 [SMILES: COc1ccc(Cl)cc1NC(=O)CN1CCc2nc3ccccc3c(N3CCN(CCO)CC3)c2C1] | N-(5-Chloro-2-methoxyphenyl)-2-{10-[4-(2-hydroxy-ethyl)piperazin-1-yl]-3,4-dihydro-1H-benzo[b]-1,6-naph-thyridin-2-yl}-acetamide |
| 11 | 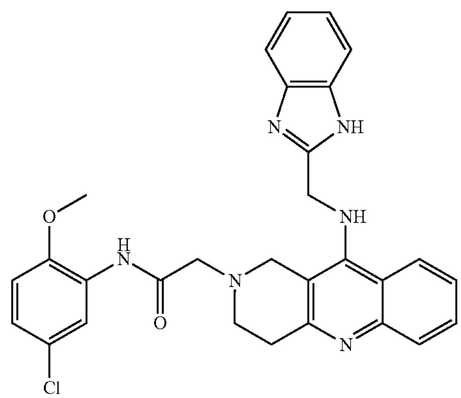 [SMILES: COc1ccc(Cl)cc1NC(=O)CN1CCc2nc3ccccc3c(NCc3nc4ccccc4[nH]3)c2C1] | 2-{10-[(1H-Benzimidazol-2-ylmethyl)amino]-3,4-dihydro-1H-benzo[b]-1,6-naphthyridin-2-yl}-N-(5-chloro-2-methoxyphenyl)-acetamide |
| 12 | 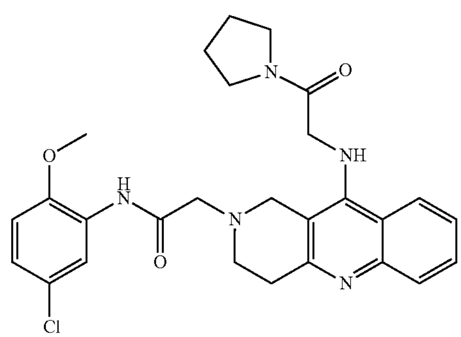 [SMILES: COc1ccc(Cl)cc1NC(=O)CN1CCc2nc3ccccc3c(NCC(=O)N3CCCC3)c2C1] | N-(5-Chloro-2-methoxyphenyl)-2-[10-(2-oxo-2-pyrrolidin-1-ylethylamino)-3,4-dihydro-1H-benzo[b]-1,6-naphthyridin-2-yl]-acetamide |
| 13 | 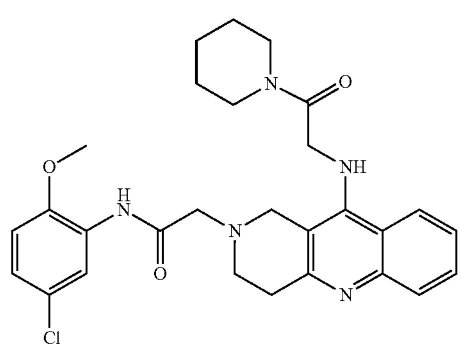 [SMILES: COc1ccc(Cl)cc1NC(=O)CN1CCc2nc3ccccc3c(NCC(=O)N3CCCCC3)c2C1] | N-(5-Chloro-2-methoxyphenyl)-2-[10-(2-oxo-2-piperidin-1-ylethylamino)-3,4-dihydro-1H-benzo[b]-1,6-naphthyridin-2-yl]-acetamide |

-continued

| Compound No. | Chemical Structure | Chemical Name |
|---|---|---|
| 14 | 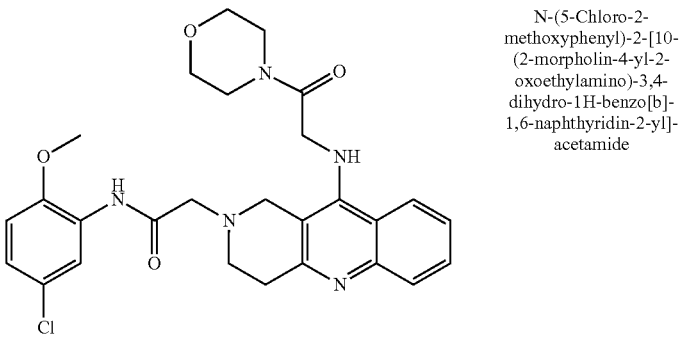 | N-(5-Chloro-2-methoxyphenyl)-2-[10-(2-morpholin-4-yl-2-oxoethylamino)-3,4-dihydro-1H-benzo[b]-1,6-naphthyridin-2-yl]-acetamide |
| 15 | 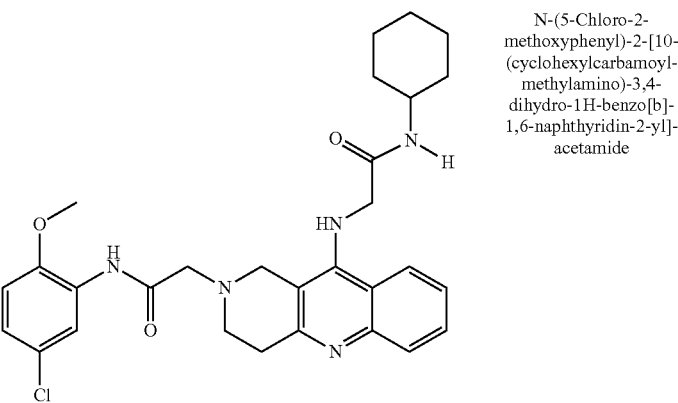 | N-(5-Chloro-2-methoxyphenyl)-2-[10-(cyclohexylcarbamoyl-methylamino)-3,4-dihydro-1H-benzo[b]-1,6-naphthyridin-2-yl]-acetamide |
| 16 | 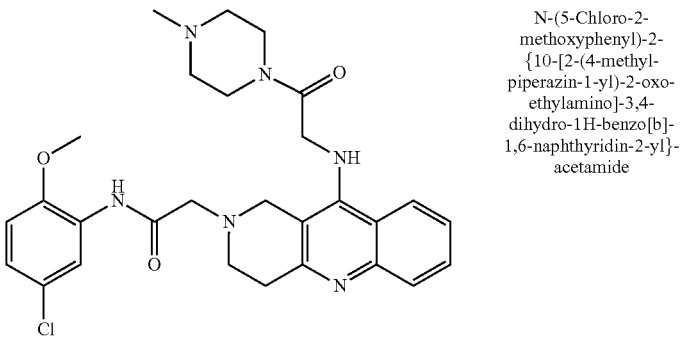 | N-(5-Chloro-2-methoxyphenyl)-2-{10-[2-(4-methyl-piperazin-1-yl)-2-oxo-ethylamino]-3,4-dihydro-1H-benzo[b]-1,6-naphthyridin-2-yl}-acetamide |
| 17 | 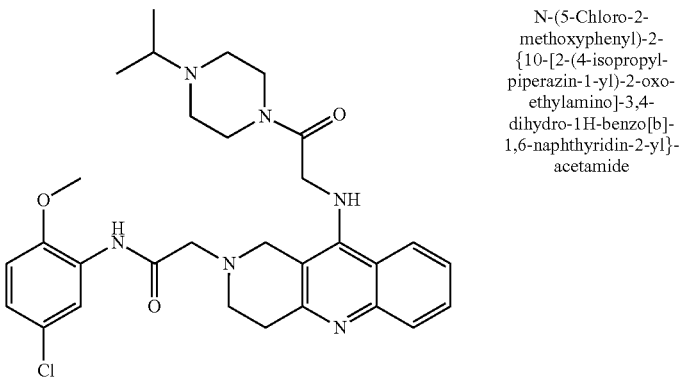 | N-(5-Chloro-2-methoxyphenyl)-2-{10-[2-(4-isopropyl-piperazin-1-yl)-2-oxo-ethylamino]-3,4-dihydro-1H-benzo[b]-1,6-naphthyridin-2-yl}-acetamide |

-continued

| Compound No. | Chemical Structure | Chemical Name |
|---|---|---|
| 18 | 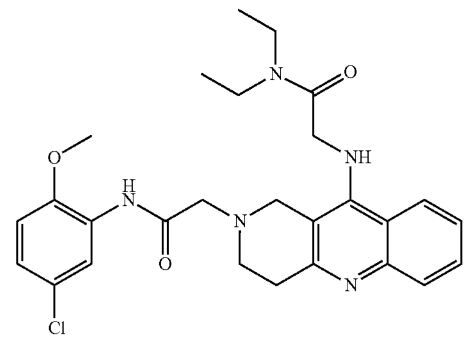 [SMILES: CCN(CC)C(=O)CNc1c2c(nc3ccccc13)CCN(CC(=O)Nc1cc(Cl)ccc1OC)C2] | N-(5-Chloro-2-methoxyphenyl)-2-[10-(diethylcarbamoyl-methylamino)-3,4-dihydro-1H-benzo[b]-1,6-naphthyridin-2-yl]-acetamide |
| 19 | 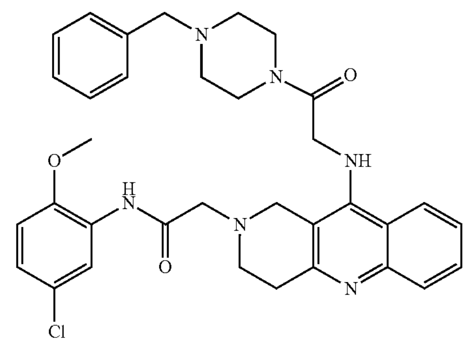 [SMILES: COc1ccc(Cl)cc1NC(=O)CN1CCc2nc3ccccc3c(NCC(=O)N3CCN(Cc4ccccc4)CC3)c2C1] | 2-{10-[2-(4-Benzyl-piperazin-1-yl)-2-oxo-ethylamino]-3,4-dihydro-1H-benzo[b]-1,6-naphthyridin-2-yl}-N-(5-chloro-2-methoxyphenyl)-acetamide |
| 20 | 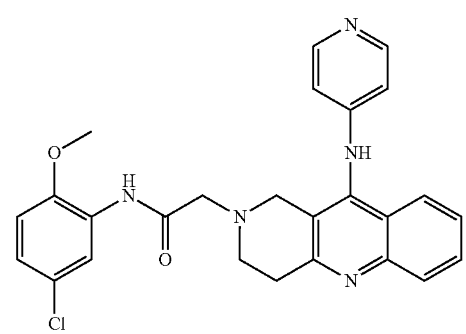 [SMILES: COc1ccc(Cl)cc1NC(=O)CN1CCc2nc3ccccc3c(Nc3ccncc3)c2C1] | N-(5-Chloro-2-methoxyphenyl)-2-[10-(pyridin-4-ylamino)-3,4-dihydro-1H-benzo[b]-1,6-naphthyridin-2-yl]-acetamide |
| 21 | 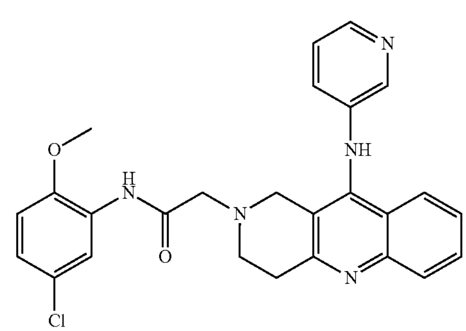 [SMILES: COc1ccc(Cl)cc1NC(=O)CN1CCc2nc3ccccc3c(Nc3cccnc3)c2C1] | N-(5-Chloro-2-methoxyphenyl)-2-[10-(pyridin-3-ylamino)-3,4-dihydro-1H-benzo[b]-1,6-naphthyridin-2-yl]-acetamide |

| Compound No. | Chemical Structure | Chemical Name |
|---|---|---|
| 22 | 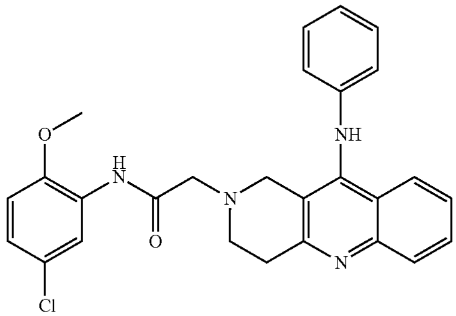 [SMILES: COc1ccc(Cl)cc1NC(=O)CN1CCc2nc3ccccc3c(Nc3ccccc3)c2C1] | N-(5-Chloro-2-methoxyphenyl)-2-(10-phenylamino-3,4-dihydro-1H-benzo[b]-1,6-naphthyridin-2-yl)-acetamide |
| 23 | 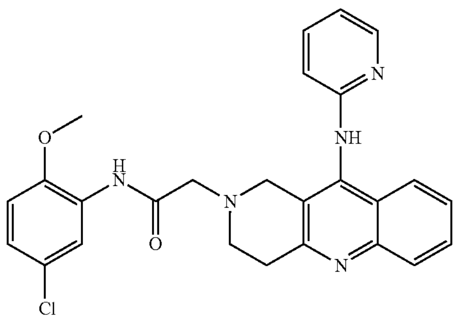 [SMILES: COc1ccc(Cl)cc1NC(=O)CN1CCc2nc3ccccc3c(Nc3ccccn3)c2C1] | N-(5-Chloro-2-methoxyphenyl)-2-[10-(pyridin-2-ylamino)-3,4-dihydro-1H-benzo[b]-1,6-naphthyridin-2-yl]-acetamide |
| 24 | | N-(5-Chloro-2-methoxyphenyl)-2-[10-(4-methoxyphenylamino)-3,4-dihydro-1H-benzo[b]-1,6-naphthyridin-2-yl]-acetamide | and pharmaceutically usable salts, solvates and stereoisomers thereof, including mixtures thereof in all ratios.

In order to avoid doubt, if chemical name and chemical structure of the compounds depicted above mistakenly do not correspond, the chemical structure is regarded as the unambiguous definition of the compound.

All the above generically or explicitly disclosed compounds, including preferred subsets/embodiments of the formula (I) disclosed here and compounds 1 to 24, are referred to below as compounds of the (present) invention or compounds according to the invention.

The nomenclature used here for the definition of compounds, in particular the compounds according to the invention, is in general based on the rules of the IUPAC organisation for chemical compounds and in particular organic compounds.

The expressions indicated for explanation of the above compounds of the invention are always, unless indicated otherwise in the description or claims, the following meanings:

The expression "unsubstituted" means that the corresponding radical, the corresponding group or the corresponding moiety has no substituents.

The expression "substituted" means that the corresponding radical, the corresponding group or the corresponding moiety has one or more substituents. Where a radical has a plurality of substituents, and a selection of various substituents is indicated, the substituents are selected independently of one another and need not be identical.

For the purposes of this invention, the expressions "alkyl" or "A" as well as other groups having the prefix "alk" relate to acyclic saturated or unsaturated hydrocarbon radicals, which may be branched or straight-chain and preferably have 1 to 8 carbon atoms, i.e. $C_1$-$C_8$-alkanyls, $C_2$-$C_8$-alkenyls and $C_2$-$C_8$-alkynyls. Alkenyls have at least one C—C double bond and alkynyls at least one C—C triple bond. Alkynyls may additionally also have at least one C—C double bond. Examples of suitable alkyl radicals are methyl, ethyl, n-propyl, isopropyl, n-butyl, isobutyl, sec-butyl, tert-butyl, n-pentyl, isopentyl, neo-pentyl, tert-pentyl, 2- or 3-methyl-pentyl, n-hexyl, 2-hexyl, isohexyl, n-heptyl, n-octyl, n-nonyl, n-decyl, n-undecyl, n-dodecyl, n-tetradecyl, n-hexadecyl, n-octadecyl, n-icosanyl, n-docosanyl, ethylenyl (vinyl), propenyl (—$CH_2CH=CH_2$; —CH=CH—$CH_3$, —C(=$CH_2$)—$CH_3$), butenyl, pentenyl, hexenyl, heptenyl, octenyl, octadienyl, octadecenyl, octadec-9-enyl, icosenyl, icos-11-enyl, (Z)-icos-11-enyl, docosnyl, docos-13-enyl, (Z)-docos-13-enyl, ethynyl, propynyl (—$CH_2$—C≡CH, —C≡C—$CH_3$), butynyl, pentynyl, hexynyl, heptynyl, octynyl. Particular preference is given to $C_{1-4}$-alkyl. A $C_{1-4}$-alkyl radical is, for example, a methyl, ethyl, propyl, isopropyl, butyl, isobutyl, tert-butyl.

For the purposes of this invention, the expression "($C_9$-$C_{30}$)alkyl" relates to acyclic saturated or unsaturated hydrocarbon radicals, which may be branched or straight-chain and have 9 to 30 carbon atoms, i.e. $C_{9-30}$-alkanyls, $C_{9-30}$-alkenyls and $C_{9-30}$-alkynyls. $C_{9-30}$-Alkenyls have at least one C—C double bond and $C_{9-30}$-alkynyls at least one C—C triple bond. $C_{9-30}$-Alkynyls may additionally also have at least one C—C double bond. Examples of suitable ($C_9$-$C_{30}$)alkyl radicals are tetradecyl, hexadecyl, octadecyl, eicosanyl, cis-13-docosenyl (erucyl), trans-13-docosenyl (brassidyl), cis-15-tetracosenyl (nervonyl) and trans-15-tetracosenyl.

For the purposes of this invention, the expression "cycloalkyl" or "Cyc" relates to saturated and partially unsaturated non-aromatic cyclic hydrocarbon groups/radicals, having 1 to 3 rings, which contain 3 to 20, preferably 3 to 12, particularly preferably 3 to 8 carbon atoms. The cycloalkyl radical may also be part of a bi- or polycyclic system, where, for example, the cycloalkyl radical is fused to an aryl, heteroaryl or heterocyclyl radical as defined here via any possible and desired ring member(s). The bonding to the compounds of the general formula can be effected via any possible ring member of the cycloalkyl radical. Examples of suitable cycloalkyl radicals are cyclopropyl, cyclobutyl, cyclopentyl, cyclohexyl, cycloheptyl, cyclooctyl, cyclodecyl, cyclohexenyl, cyclopentenyl and cyclooctadienyl. Particular preference is given to $C_3$-$C_9$-cycloalkyl and $C_4$-$C_8$-cycloalkyl. A $C_4$-$C_8$-cycloalkyl radical is, for example, a cyclobutyl, cyclopentyl, cyclohexyl, cycloheptyl, cyclooctyl.

For the purposes of this invention, the expression "heterocyclyl" relates to a mono- or polycyclic system having 3 to 20, preferably 5 or 6 to 14 ring atoms comprising carbon atoms and 1, 2, 3, 4, or 5 heteroatoms, in particular nitrogen, oxygen and/or sulfur, which are identical or different. The cyclic system may be saturated, mono- or polyunsaturated, but cannot be aromatic. In the case of a cyclic system consisting of at least two rings, the rings may be fused or spiro- or otherwise connected. Such "heterocyclyl" radicals may be linked via any desired ring member. The expression "heterocyclyl" also includes systems in which the heterocycle is part of a bi- or polycyclic saturated, partially unsaturated and/or aromatic system, as is the case if the heterocycle is fused to an "aryl", "cycloalkyl", "heteroaryl" or "heterocyclyl" group as defined here via any desired and possible ring member of the heterocycyl radical. The bonding to the compounds of the general formula can be effected via any possible ring member of the heterocyclyl radical. Examples of suitable "heterocyclyl" radicals are pyrrolidinyl, thiapyrrolidinyl, piperidinyl, piperazinyl, oxapiperazinyl, oxapiperidinyl, oxadiazolyl, tetrahydrofuryl, imidazolidinyl, thiazolidinyl, tetrahydropyranyl, morpholinyl, tetrahydrothiophenyl, dihydropyranyl, indolinyl, indolinylmethyl, imidazolidinyl, 2-azabicyclo[2.2.2]octanyl.

For the purposes of this invention, the expression "aryl" relates to a mono- or polycyclic aromatic hydrocarbon systems having 3 to 14, preferably 5 to 14, particularly preferably 6 to 10 carbon atoms. The expression "aryl" also includes systems in which the aromatic ring is part of a bi- or polycyclic saturated, partially unsaturated and/or aromatic system, such as where the aromatic cycle is fused to an "aryl", "cycloalkyl", "heteroaryl" or "heterocyclyl" group as defined here via any desired and possible ring member of the aryl radical. The bonding to the compounds of the general formula can be effected via any possible ring member of the aryl radical. Examples of suitable "aryl" radicals are phenyl, biphenyl, naphthyl, 1-naphthyl, 2-naphthyl and anthracenyl, but also indanyl, indenyl, or 1,2,3,4-tetrahydronaphthyl. The particularly preferred aryl is phenyl.

Ar preferably denotes phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-methoxyphenyl, o-, m- or p-nitrophenyl, o-, m- or p-aminophenyl, o-, m- or p-(N-methylamino)phenyl, o-, m- or p-(N-methylaminocarbonyl)phenyl, o-, m- or p-acetamidophenyl, o-, m- or p-methoxyphenyl, o-, m- or p-ethoxyphenyl, o-, m- or p-ethoxycarbonylphenyl, o-, m- or p-(N,N-dimethylamino)phenyl, o-, m- or p-(N,N-dimethylaminocarbonyl)phenyl, o-, m- or p-(N-ethylamino)phenyl, o-, m- or p-(N,N-diethylamino)phenyl, o-, m- or p-fluorophenyl, o-, m- or p-bromophenyl, o-, m- or p-chlorophenyl, o-, m- or p-(methylsulfonamido)phenyl, o-, m- or p-(methylsulfonyl)phenyl, furthermore preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxyphenyl, 3-nitro-4-chlorophenyl, 3-amino-4-chloro-, 2-amino-3-chloro-, 2-amino-4-chloro-, 2-amino-5-chloro- or 2-amino-6-chlorophenyl, 2-nitro-4-N,N-dimethylamino- or 3-nitro-4-N,N-dimethylaminophenyl, 2,3-diaminophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 3,6-dichloro-4-aminophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl, 3-chloro-4-acetamidophenyl, 3-fluoro-4-methoxyphenyl, 3-amino-6-methylphenyl, 3-chloro-4-acetamidophenyl, 2,5-dimethyl-4-chlorophenyl, naphthyl or biphenyl.

Ar furthermore preferably denotes phenyl, indanyl, naphthyl or biphenyl, each of which is unsubstituted or mono-, di-, tri-, tetra- or pentasubstituted by Hal, A and/or $(CRR)_qOR$.

For the purposes of this invention, the expression "heteroaryl" relates to a 3- to 15-, preferably 5- to 14-, more preferably 5-, 6- or 7-membered mono- or polycyclic aromatic hydrocarbon radical which contains at least 1, optionally also 2, 3, 4 or 5 heteroatoms, preferably nitrogen, oxygen and/or sulfur, where the heteroatoms are identical or different. The number of nitrogen atoms is preferably 0, 1, 2, or 3, and the number of oxygen and sulfur atoms is, independently, 0 or 1. The expression "heteroaryl" also includes systems in which the aromatic ring is part of a bi- or polycyclic saturated, partially unsaturated and/or aromatic system, as is the case if the aromatic ring is fused to an "aryl", "cycloalkyl", "heteroaryl" or "heterocyclyl" group as defined here via any desired and possible ring member of the heteroaryl radical. The bonding to the compounds of the general formula can be effected via any possible ring member of the heteroaryl radical. Examples of suitable "heteroaryl" are acridinyl, benzdioxinyl, benzimidazolyl, benzisoxazolyl, benzodioxolyl, benzofuranyl, benzothiadiazolyl, benzothiazolyl, benzothienyl, benzoxazolyl, carbazolyl, cinnolinyl, dibenzofuranyl, dihydrobenzothienyl, furanyl, furazanyl, furyl, imidazolyl, indazolyl, indolinyl, indolizinyl, indolyl, isobenzylfuranyl, isoindolyl, isoquinolinyl, isoquinolyl, isothiazolyl, isoxazolyl, naphthyridinyl, oxadiazolyl, oxazolyl, phenazinyl, phenothiazinyl, phenoxazinyl, phthalazinyl, pteridinyl, purinyl, pyrazinyl, pyrazolyl, pyridazinyl, pyridinyl, pyridyl, pyrimidinyl, pyrimidyl, pyrrolyl, quinazolinyl, quinolinyl, quinolyl, quinoxalinyl, tetrazolyl, thiadiazolyl, thiazolyl, thienyl, thiophenyl, triazinyl, triazolyl.

Irrespective of further substitutions, Het denotes, for example, 2- or 3-furyl, 2- or 3-thienyl, 1-, 2- or 3-pyrrolyl, 1-, 2,4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, indazolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, further preferably 1,3-benzodioxol-5-yl, 1,4-benzodioxan-6-yl, 2,1,3-benzothiadiazol-4-, -5-yl or 2,1,3-benzoxadiazol-5-yl or dibenzofuranyl.

The heterocyclic radicals may also be partially or fully hydrogenated. Irrespective of further substitutions, Het can thus also denote, for example, 2,3-dihydro-2-, -3-, -4- or -5-furyl, 2,5-dihydro-2-, -3-, -4- or 5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3, 4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, furthermore preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or 6-yl, 2,3-(2-oxomethylenedioxy) phenyl or also 3,4-dihydro-2H-1,5-benzodioxepin-6- or -7-yl, furthermore preferably 2,3-dihydrobenzofuranyl, 2,3-dihydro-2-oxofuranyl, 3,4-dihydro-2-oxo-1H-quinazolinyl, 2,3-dihydrobenzoxazolyl, 2-oxo-2,3-dihydrobenzoxazolyl, 2,3-dihydrobenzimidazolyl, 1,3-dihydroindole, 2-oxo-1,3-dihydroindole or 2-oxo-2,3-dihydrobenzimidazolyl.

Het furthermore preferably denotes a monocyclic saturated, unsaturated or aromatic heterocycle having 1 to 4 N, O and/or S atoms, which may be unsubstituted or mono-, di- or trisubstituted by A, Ar, $(CRR)_q$Het and/or $(CRR)_q$OR.

Het very particularly preferably denotes piperidinyl, piperazinyl, pyrrolidinyl, morpholinyl, furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl or pyrazinyl, each of which is unsubstituted or mono- or disubstituted by A, Ar, $(CRR)_q$Het and/or $(CRR)_q$OR.

For the purposes of the present invention, the expressions "alkyl-cycloalkyl", "cycloalkylalkyl", "alkyl-heterocyclyl", "heterocyclylalkyl", "alkyl-aryl", "arylalkyl", "alkyl-heteroaryl" and "heteroarylalkyl" indicate that alkyl, cycloalkyl, heterocyclyl, aryl and heteroaryl are each as defined here, and the cycloalkyl, heterocyclyl, aryl and heteroaryl radical is bonded to the compounds of the general formula via an alkyl radical, preferably $C_1$-$C_8$-alkyl radical, particularly preferably $C_1$-$C_4$-alkyl radical.

For the purposes of this invention, the expression "alkyloxy" or "alkoxy" relates to an alkyl radical in accordance with the above definition which is bonded to an oxygen atom. The bonding to the compounds of the general formula takes place via the oxygen atom. Examples are methoxy, ethoxy and n-propyloxy, propoxy, isopropoxy. Preference is given to "$C_1$-$C_4$-alkyloxy" having the indicated number of carbon atoms.

For the purposes of this invention, the expression "cycloalkyloxy" or "cycloalkoxy" relates to a cycloalkyl radical in accordance with the above definition which is bonded to an oxygen atom. The bonding to the compounds of the general formula takes place via the oxygen atom. Examples are cyclopropyloxy, cyclobutyloxy, cyclopentyloxy, cyclohexyloxy, cycloheptyloxy, cyclooctyloxy. Preference is given to "$C_3$-$C_9$cycloalkyloxy" having the indicated number of carbon atoms.

For the purposes of this invention, the expression "heterocyclyloxy" relates to a heterocyclyl radical in accordance with the above definition which is bonded to an oxygen atom. The bonding to the compounds of the general formulae takes place via the oxygen atom. Examples are pyrrolidinyloxy, thiapyrrolidinyloxy, piperidinyloxy, piperazinyloxy.

For the purposes of this invention, the expression "aryloxy" relates to an aryl radical in accordance with the above definition which is bonded to an oxygen atom. The bonding to the compounds of the general formula takes place via the oxygen atom. Examples are phenyloxy, 2-naphthyloxy, 1-naphthyloxy, biphenyloxy, indanyloxy. Preference is given to phenyloxy.

For the purposes of this invention, the expression "heteroaryloxy" relates to a heteroaryl radical in accordance with the above definition which is bonded to an oxygen atom. The bonding to the compounds of the general formula takes place via the oxygen atom. Examples are pyrrolyloxy, thienyloxy, furyloxy, imidazolyloxy, thiazolyloxy.

For the purposes of this invention, the expression "carbonyl" or "carbonyl moiety" relates to a —C(O)— group.

For the purposes of this invention, the expression "alkylcarbonyl" relates to a "alkyl-C(O)—" group, in which alkyl is as defined here.

The expression "alkoxycarbonyl" or "alkyloxycarbonyl" relates to a "alkyl-O—C(O)—" group, in which alkyl is as defined here.

For the purposes of this invention, the expression "alkoxyalkyl" relates to a "alkyl-O-alkyl-" group, in which alkyl is as defined here.

For the purposes of this invention, the expression "haloalkyl" relates to an alkyl group as defined here which contains at least one carbon atom which is substituted by at least one halogen as defined here.

For the purposes of this invention, the expression "halogen", "halogen atom", "halogen substituent" or "Hal" relates to one or optionally a plurality of fluorine (F, fluoro), bromine (Br, bromo), chlorine (Cl, chloro), or iodine (I, iodo) atoms. The designations "dihalogen", "trihalogen" and "perhalogen" relate to two, three and four substituents respectively, where each substituent can be selected independently from the group consisting of fluorine, chlorine, bromine and iodine. "Halogen" preferably denotes a fluorine, chlorine or bromine atom. Fluorine is particularly preferred if the halogens on an alkyl (haloalkyl) or alkoxy group (for example $CF_3$ and $CF_3O$) are substituted.

The expression "hydroxyl" or "hydroxy" means an OH group.

For the purposes of this invention, the expression "composition", for example in pharmaceutical composition, is intended to encompass a product comprising the active compound(s), and the inert ingredient(s) which make up the excipient, as well as any desired product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any desired compositions which bare prepared by mixing a compound of the present invention and a pharmaceutically acceptable excipient.

The expressions "administration of" and "administering a" compound should be taken to mean that a compound of the invention or a prodrug of a compound of the invention is made available to the individual needs.

Thus, as used here, the expression "effective amount" means any amount of a medicament or pharmaceutical agent which causes the biological or medical response that is being sought, for example by a researcher or clinician, in a tissue, system, animal or human. Furthermore, the expression "therapeutically effective amount" means any desired amount which, compared with a corresponding subject who has not received this amount, results in improved treatment, healing, prevention, or amelioration of a disease, disorder, or side effect, or a decrease in the rate of advancement of a disease or disorder. The expression also encompasses within its scope amounts the amounts which are effective in enhancing normal physiological function.

Compounds of the formula (I) also mean their pharmaceutically usable derivatives, optically active forms (stereoisomers), tautomers, polymorphs, enantiomers, racemates, diastereomers and the hydrates and solvates of these compounds. Solvates of the compounds are taken to mean adductions of inert solvent molecules onto the compounds, which form owing to their mutal attractive force. Solvates are, for example, mono- or dihydrates or alcoholates. Pharmaceutically usable derivatives are taken to mean, for example, the salts of the compounds according to the invention and also so-called prodrug compounds.

The invention also relates to the use of mixtures of the compounds of the formula (I), for example mixtures of two diastereomers, for example in the ratio 1:1, 1:2, 1:3, 1:4, 1:5, 1:10, 1:100 or 1:1000. These are particularly preferably mixtures of stereoisomeric compounds.

All stereoisomers of the compounds of the invention are considered, either as a mixture or in pure or essentially pure form. The compounds of the invention may have centres of asymmetry on any of the carbon atoms. Consequently, they can exist in the form of their racemates, in the form of the pure enantiomers and/or diastereomers or in the form of mixtures of these enantiomers and/or diastereomers. The mixtures may have any desired mixing ratio of the stereoisomers.

Thus, for example, the compounds of the invention which have one or more centres of chirality and which are in the form of racemates or diastereomer mixtures can be fractionated by methods known per se into their optical pure isomers, i.e. enantiomers or diastereomers. The compounds of the invention can be separated by column separation on chiral or non-chiral phases or by recrystallisation from an optionally optically active solvent or using an optically active acid or base or by derivatisation with an optically active reagent, such as, for example, an optically active alcohol, and subsequent elimination of the radical.

The compounds of the invention may be present in the form of their double-bond isomers as "pure" E or Z isomers or in the form of mixtures of these double-bond isomers.

Where possible, the compounds of the invention may be in the form of the tautomers, such as keto-enol tautomers.

It is also possible for the compounds of the invention to be in the form of any desired prodrugs, such as, for example, esters, carbonates, carbamates, ureas, amides or phosphates, where, in these cases, the actually biologically active form is only released through metabolism. Any compound which can be converted in vivo to provide the bioactive agent (i.e. compounds of the invention) is a prodrug within the scope and spirit of the invention.

Various forms of prodrugs are well known in the art and are described, for example, in:
(i) Wermuth C G et al., Chapter 31: 671-696, The Practice of Medicinal Chemistry, Academic Press 1996;
(ii) Bundgaard H, Design of Prodrugs, Elsevier 1985; and
(iii) Bundgaard H, Chapter 5: 131-191, A Textbook of Drug Design and Development, Harwood Academic Publishers 1991.

These references are incorporated herein by way of reference.

It is furthermore known that chemical substances are converted in the body into metabolites which may, where appropriate, likewise elicit the desired biological effect—under some circumstances even in more pronounced form.

Any biologically active compound which has been converted in vivo by metabolism from any of the compounds of the invention is a metabolite within the scope and spirit of the invention.

The compounds of the invention can, if they contain a sufficiently basic group, such as, for example, a secondary or tertiary amine, be converted into salts using inorganic and organic acids. The pharmaceutically acceptable salts of the compounds of the invention are preferably formed with hydrochloric acid, hydrobromic acid, iodic acid, sulfuric acid, phosphoric acid, methanesulfonic acid, p-toluenesulfonic acid, carbonic acid, formic acid, acetic acid, sulfoacetic acid, trifluoroacetic acid, oxalic acid, malonic acid, maleic acid, succinic acid, tartaric acid, racemic acid, malic acid, embonic acid, mandelic acid, fumaric acid, lactic acid, citric acid, taurocholic acid, glutaric acid, stearic acid, glutamic acid or aspartic acid. The salts formed are, inter alia, hydrochlorides, chlorides, hydrobromides, bromides, iodides, sulfates, phosphates, methanesulfonates, tosylates, carbonates, bicarbonates, formates, acetates, sulfoacetates, triflates, oxalates, malonates, maleates, succinates, tartrates, malates, embonates, mandelates, fumarates, lactates, citrates, glutarates, stearates, aspartates and glutamates. The stoichiometry of the salts formed from the compounds of the invention may, in addition, be an integral or non-integral multiple of one.

The compounds of the invention can, if they contain a sufficiently acidic group, such as, for example, the carboxyl, sulfonic acid, phosphoric acid or a phenolic group, be converted into their physiologically tolerated salts using inorganic and organic bases. Examples of suitable inorganic bases are ammonia, sodium hydroxide, potassium hydroxide, calcium hydroxide, and examples of suitable organic bases are ethanolamine, diethanolamine, triethanolamine, ethylenediamine, t-butylamine, t-octylamine, dehydroabietylamine, cyclohexylamine, dibenzylethylenediamine and lysine. The stoichiometry of the salts formed from the compounds of the invention may, in addition, be an integral or non-integral multiple of one.

It is also possible for the compounds of the invention to be in the form of their solvates and, in particular, hydrates, which can be obtained, for example, by crystallisation from a solvent or from aqueous solution. It is also possible for one, two, three or any number of solvate or water molecules to combine with the compounds of the invention to give solvates and hydrates.

The expression "solvate" denotes a hydrate, an alcoholate or another solvate of crystallisation.

It is known that chemical substances form solids which exist in different order states which are referred to as polymorphic forms or modifications. The various modifications of a polymorphic substance may differ greatly in their physical properties. The compounds of the invention can exist in various polymorphic forms and certain modifications may, in addition, be metastable. All these polymorphic forms of the compounds are to be regarded as being part of the invention.

The compounds of the invention are, surprisingly, distinguished by strong and/or selective inhibition of autotaxin.

Owing to their surprisingly strong and/or selective enzyme inhibition, the compounds of the invention can advantageously be administered at lower doses compared with other less potent or selective inhibitors of the prior art while still achieving equivalent or even superior desired biological effects. In addition, such a dose reduction may advantageously lead to fewer or even no medicinal adverse effects. Furthermore, the high inhibition selectivity of the compounds of the invention may translate into a decrease in undesired side effects on its own, irrespective of the dose used.

As autotaxin inhibitors, the compounds of the invention generally have an inhibition constant $IC_{50}$ of less than about 30 μM, and preferably less than about 10 μM.

The object of the present invention has surprisingly been achieved in a further aspect by the provision of the use of a compound of the invention as autotaxin inhibitor.

For the purposes of the present invention, the expressions "inhibiting, inhibition and/or retardation" are intended to relate to the following: "partial or complete inhibiting, inhibition and/or retardation". In this case, it is within the specialist knowledge of the average person skilled in the art to measure and determine such inhibiting, inhibition, and/or retardation using the standard measurement and determination methods. Thus, partial inhibiting, inhibition and/or retardation, for example, can be measured and determined in relation to complete inhibiting, inhibition and/or retardation.

The object of the present invention has surprisingly been achieved in a further aspect by provision of a process for the preparation of a compound of the invention and pharmaceutically usable salts, solvates and stereoisomers thereof, characterised in that a compound of the formula (II)

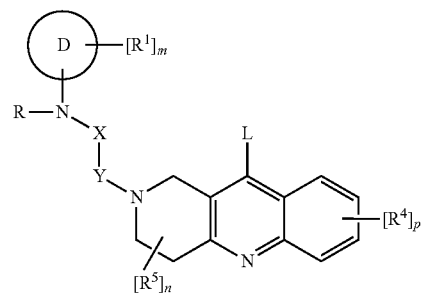

in which D, X, Y, R, $R^1$, $R^4$, $R^5$, m, n and p have the indicated meanings defined here and L is a halogen, tosylate, mesylate or triflate, is reacted with a compound of the formula (III)

H—$NR^2R^3$ (III)

in which $R^2$, $R^3$ have the indicated meanings defined here, and/or a base or acid of the resultant compounds of the formula (I) as defined here is converted into one of its salts, or characterised in that a compound of the formula (IV)

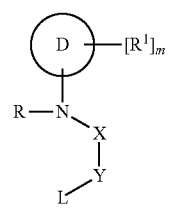

in which D, X, Y, R, $R^1$ and m have the indicated meanings defined here and L represents a halogen, tosylate, mesylate, triflate or a free or reactively modified OH group, such as, for example, an activated ester, an imidazolide or alkylsulfonyloxy having 1-6 C atoms (preferably methylsulfonyloxy or trifluoromethylsulfonyloxy) or arylsulfonyloxy having 6-10 C atoms (preferably phenyl- or p-tolylsulfonyloxy), is reacted with a compound of the formula (V)

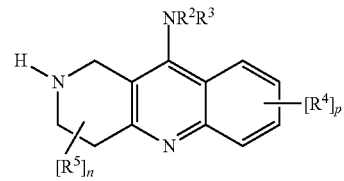

in which $R^2$, $R^3$, $R^4$, $R^5$, n and p have the indicated meanings defined here, and/or a base or acid of the resultant compounds of the formula (I) as defined here is converted into one of its salts, or
characterised in that a compound of the formula (VI)

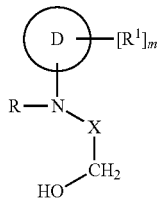

(VI)

in which D, X, R, R$^1$ and m have the indicated meanings defined here,
is firstly reacted with a carbonylation agent, for example 1,1'-carbonyl-diimidazole, phosgene, diphosgene, triphosgene, urea and dialkyl carbonate, preferably 1,1'-carbonyldiimidazole,
and then reacted with a compound of the formula (V)

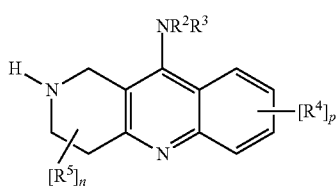

(V)

in which R$^2$, R$^3$, R$^4$, R$^5$, n and p have the indicated meanings defined here,
and/or a base or acid of the resultant compounds of the formula (I) as defined here is converted into one of its salts.

A reactively modified OH group, such as, for example, an activated ester, an imidazolide or alkylsulfonyloxy having 1-6 C atoms (preferably methylsulfonyloxy or trifluoromethylsulfonyloxy) or arylsulfonyloxy having 6-10 C atoms (preferably phenyl- or p-tolylsulfonyloxy): radicals of this type for activation of the carboxyl group in typical acylation reactions are described in the literature (for example in the standard works, such as Houben-Weyl, Methoden der organischen Chemie [Methods of Organic Chemistry], Georg-Thieme-Verlag, Stuttgart). Activated esters are advantageously formed in situ, for example by addition of HOBt or N-hydroxysuccinimide.

All crude products were subjected to standard chromatography using solvent mixtures comprising methanol, ethanol, isopropanol, n-hexane, cyclohexane or petrol ether.

A more detailed description of the preparation processes can also be found in the examples and the following general description of the preferred conditions.

A physiologically acceptable salt of a compound of the invention can also be obtained by isolation and/or treatment of the compound of the invention obtained by the reaction described with an acid or a base.

The compounds of the invention and also the starting materials for their preparation are prepared by methods as described in the examples or by methods known per se, as described in the literature (for example in standard works, such as Houben-Weyl, Methoden der Organischen Chemie [Methods of Organic Chemistry], Georg Thieme Verlag, Stuttgart; Organic Reactions, John Wiley & Sons, Inc., New York), to be precise under reaction conditions which are known and suitable for the said reactions. Use can also be made here of variants which are known per se, but are not mentioned here in greater detail.

The starting materials for the claimed process may, if desired, also be formed in situ by not isolating them from the reaction mixture, but instead immediately converting them further into the compounds of the invention. On the other hand, it is possible to carry out the reaction stepwise.

The reaction of the compounds is preferably carried out in the presence of a suitable solvent, which is preferably inert under the respective reaction conditions. Examples of suitable solvents are hydrocarbons, such as hexane, petroleum ether, benzene, toluene or xylene; chlorinated hydrocarbons, such as trichloroethylene, 1,2-dichloroethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether or ethylene glycol dimethyl ether (diglyme); ketones, such as acetone or butanone; amides, such as acetamide, dimethylacetamide, dimethylformamide (DMF) or N-methylpyrrolidinone (NMP); nitriles, such as acetonitrile; sulfoxides, such as dimethyl sulfoxide (DMSO); nitro compounds, such as nitromethane or nitrobenzene; esters, such as ethyl acetate, or mixtures of the said solvents or mixtures with water. Polar solvents are generally preferred. Examples for suitable polar solvents are chlorinated hydrocarbons, alcohols, glycol ethers, nitriles, amides and sulfoxides or mixtures thereof. Particular preference is given to amides, in particular dimethylformamide (DMF).

As indicated above, the reaction temperature is between about −100° C. and 300° C., depending on the reaction step and the conditions used.

The reaction times are generally in the range between a few minutes and several days, depending on the reactivity of the respective compounds and the respective reaction conditions. Suitable reaction times can easily be determined by methods known in the art, for example reaction monitoring. Based on the reaction temperatures given above, suitable reaction times are generally in the range between 10 min and 48 h.

The starting compounds of the formulae (II), (III), (IV), (V) and (VI) are generally known. If they are novel, however, they can be prepared by methods known per se. The starting materials are generally also commercially available.

A base of a compound of the invention can be converted into the associated acid-addition salt using an acid, for example by reaction of equivalent amounts of the base and the acid in a preferably inert solvent, such as ethanol, followed by evaporation. Suitable acids for this reaction are, in particular, those which give physiologically acceptable salts. Thus, it is possible to use inorganic acids, for example sulfuric acid, sulfurous acid, dithionic acid, nitric acid, hydrohalic acids, such as hydrochloric acid or hydrobromic acid, phosphoric acids, such as, for example, orthophosphoric acid, sulfamic acid, furthermore organic acids, in particular aliphatic, alicyclic, araliphatic, aromatic or heterocyclic monobasic or polybasic carboxylic, sulfonic or sulfuric acids, for example formic acid, acetic acid, propionic acid, hexanoic acid, octanoic acid, decanoic acid, hexadecanoic acid, octadecanoic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, trimethoxybenzoic acid, adamantanecarboxylic acid, p-toluenesulfonic acid, glycolic acid, embonic acid, chlorophenoxyacetic acid, aspartic acid, glutamic acid, proline, glyoxylic acid, palmitic acid, parachlorophenoxyisobutyric acid, cyclohexanecarboxylic acid, glucose 1-phosphate, naphthalenemono- and -disulfonic acids or laurylsulfuric acid.

Salts with physiologically unacceptable acids, for example picrates, can be used for the isolation and/or purification of the compounds of the invention.

On the other hand, compounds of the invention can be converted into the corresponding metal salts, in particular alkali-metal salts or alkaline-earth metal salts, or into the corresponding ammonium salts using bases (for example sodium hydroxide, potassium hydroxide, sodium carbonate or potassium carbonate). Suitable salts are furthermore substituted ammonium salts, for example the dimethyl-, diethyl- and diisopropylammonium salts, monoethanol-, diethanol- and diisopropanolammonium salts, cyclohexyl- and dicyclohexylammonium salts, dibenzylethylenediammonium salts, furthermore, for example, salts with arginine or lysine.

If desired, the free bases of the compounds of the invention can be liberated from their salts by treatment with strong bases, such as sodium hydroxide, potassium hydroxide, sodium carbonate or potassium carbonate, so long as no further acidic groups are present in the molecule. In the cases of compounds of the invention which contain free acid groups, salt formation can also be achieved by treatment with bases. Suitable bases are alkali-metal hydroxides, alkaline-earth metal hydroxides or organic bases in the form of primary, secondary or tertiary amines.

Each reaction step described here can optionally be followed by one or more work-up and/or isolation methods. Suitable such methods are known in the art, for example from standard works, such as Houben-Weyl, Methoden der organischen Chemie [Methods of Organic Chemistry], Georg-Thieme-Verlag, Stuttgart). Examples of such methods are, but are not limited to, evaporation of a solvent, distillation, crystallisation, fractional crystallisation, extraction methods, washing methods, digestion methods, filtration methods, chromatography, chromatography by HPLC and drying methods, in particular drying methods in vacuo and/or elevated temperature.

The object of the present invention has been achieved in a further aspect by the provision of a medicament comprising at least one compound of the invention and/or pharmaceutically usable salts, solvates and stereoisomers thereof, including mixtures thereof in all ratios, and optionally excipients and/or adjuvants.

The object of the present invention has been achieved in a further aspect by the provision of a medicament comprising at least one compound of the invention and/or pharmaceutically usable salts, solvates and stereoisomers thereof, including mixtures thereof in all ratios, for use in the treatment and/or prophylaxis of physiological and/or pathophysiological conditions in which the inhibition, regulation and/or modulation of phosphodiesterase or lysophospholipase autotaxin plays a role. This is also intended to encompass a corresponding use for the preparation of a medicament for the treatment and/or prophylaxis of the above-mentioned conditions and a method for the treatment of the said diseases comprising the administration of one or more compounds according to the invention to a patient in need of such an administration.

The object of the present invention has surprisingly been achieved in another aspect by the provision of a medicament comprising at least one compound of the invention and/or pharmaceutically usable salts, solvates and stereoisomers thereof, including mixtures thereof in all ratios, for use in the treatment and/or prophylaxis of cancer, tumours, malignant tumours, benign tumours, solid tumours, sarcomas, carcinomas, hyperproliferative diseases, carcinoids, Ewing's sarcomas, Kaposi's sarcomas, brain tumours, tumours originating from the brain and/or nervous system and/or meninges, gliomas, glioblastomas, neuroblastomas, stomach cancer, kidney cancer, kidney cell carcinomas, prostate cancer, prostate carcinomas, connective tissue tumours, soft tissue sarcomas, pancreas tumours, liver tumours, head tumours, neck tumours, laryngeal cancer, oesophageal cancer, thyroid cancer, osteosarcomas, retinoblastomas, thymus gland cancer, testicular cancer, lung cancer, lung adenocarcinomas, small-cell lung carcinomas, bronchial carcinomas, breast cancer, mammacarcinomas, intestinal cancer, colorectal tumours, colon carcinomas, rectal carcinomas, gynaecological tumours, ovarian tumours, uterine cancer, cervical cancer, cervical carcinomas, corpus carcinomas, endometrial carcinomas, urinary bladder cancer, urogenital tract cancer, bladder cancer, skin cancer, epithelial tumours, squamous epithelial carcinomas, basaliomas, spinaliomas, melanomas, intraocular melanomas, leukaemias, monocytic leukaemias, chronic leukaemias, chronic myeloid leukaemias, chronic lymphatic leukaemias, acute leukaemias, acute myeloid leukaemias, acute lymphatic leukaemias, lymphomas, angiogenesis, arteriosclerosis, atherosclerosis, eye diseases, uveittiis, choroidal neovascularisation, diabetic retinopathy, autoimmune diseases, inflammatory diseases, asthma, chronic obstructive pulmonary disease (COPD), chronic inflammatory bowel disease (IBD), arthritis, osteoporosis, osteoarthritis, gout, gouty arthritis, rheumatoid spondylitis, allergic rhinitis, psoriasis, neurodegenerative diseases, restenosis, wound healing, transplant rejection, autoimmune enteropathy, autoimmune hepatitis, autoimmune polyendocrinopathy candidiasis ectodermal dystrophy syndrome type I (APECED), bullous pemphigoid, chronic gastritis, Churg-Strauss syndrome, colitis ulcerosa, dermatomyositis, type 1 diabetes mellitus, dermatitis herpetiformis Duhring, epidermolysis bullosa acquisita, glomerulonephritis, Goodpasture's syndrome, Guillain-Barré syndrome, Hashimoto's thyreoiditis, lichen sclerosus, linear IgA dermatosis, lupus erythematodes, microscopic polyangiitis, Adamantiades-Behçet disease, Basedow's disease, Bechterew's disseease, Crohn's disseease, multiple sclerosis, myasthenia gravis, PANDAS (pediatric autoimmune neuropsychiatric disorders associated with streptococcal infections), pelvic inflammatory disease (PID), pemphigus foliaceus, pemphigus seborrhoicus, pemphigus vulgaris, polychondritis, polymyositis, rheumatic fever, rheumatoid arthritis, SAPHO syndrome, sarcoidosis (Boeck's disease), Sjögren's syndrome, dematosclerosis, stiff person syndrome, sympathetic ophthalmia, systemic lupus erythematodes, vasculitis allergica, vitiligo, Wegener's granulomatosis and/or celiac disease. A corresponding use for the preparation of a medicament for the treatment and/or prophylaxis of the above-mentioned conditions and also a method for the treatment of the said diseases comprising the administration of one or more compounds according to the invention to a patient in need of such an administration is intended to be comprised.

Compounds of the invention can be used in combination with one or more other active compounds (ingredients, medicaments) in the treatment, prevention, suppression or amelioration of diseases or conditions for which compounds of the invention or the other substances have utility. The combination of the medicaments is typically safer or more effective than the respective medicament alone, or the combination is safer or more effective than would be expected on the basis of the additive properties of the individual medicaments. A further medicament or further medicaments of this type may be administered by a route and in an amount as usually used simultaneously or sequentially with a compound of the invention. If a compound of the invention is used simultaneously with one or more further medicaments, a combination product comprising (an)other medicament(s) of this type and the compound of the invention is preferred. However, combination therapy also encompasses therapies in which the compound of the invention and one or more further medicaments are administered in accordance with different, overlapping schedules. It is considered that, on use in combination with other active compounds, the compound of the present invention or the other active compound or both can be used effectively in lower doses than when each is used alone. The pharmaceutical compositions of the present invention therefore include those which comprise one or more further active compounds besides a compound of the invention.

The examples of other active compounds (ingredients, drugs) which can be administered together with a compound of the invention, and administered either separately or in the same pharmaceutical composition, include, but are not limited to the compound classes and specific compounds listed in Table 1:

TABLE 1

| | | |
|---|---|---|
| Alkylating agents | Cyclophosphamide | Lomustine |
| | Busulfan | Procarbazine |
| | Ifosfamide | Altretamine |
| | Melphalan | Estramustine phosphate |
| | Hexamethylmelamine | Mechloroethamine |
| | Thiotepa | Streptozocin |
| | Chloroambucil | Temozolomide |
| | Dacarbazine | Semustine |
| | Carmustine | |
| Platinum agents | Cisplatin | Carboplatin |
| | Oxaliplatin | ZD-0473 (AnorMED) |
| | Spiroplatin | Lobaplatin |
| | Carboxyphthalatoplatinum | (AeternaZentaris) |
| | Tetraplatin | Satraplatin (Johnson |
| | Ormiplatin | Matthey) |
| | Iproplatin | BBR-3464 (Hoffmann-La Roche) |
| | | SM-11355 (Sumitomo) |
| | | AP-5280 (Access) |
| Antimetabolites | Azacytidine | Tomudex |
| | Gemcitabine | Trimetrexate |
| | Capecitabine | Deoxycoformycin |
| | 5-Fluorouracil | Fludarabine |
| | Floxuridine | Pentostatin |
| | 2-Chlorodesoxyadenosine | Raltitrexed |
| | 6-Mercaptopurine | Hydroxyurea |
| | 6-Thioguanine | Decitabine (SuperGen) |
| | Cytarabine | Clofarabine (Bioenvision) |
| | 2-Fluorodesoxycytidine | Irofulven (MGI Pharma) |
| | Methotrexate | DMDC (Hoffmann-La Roche) |
| | Idatrexate | Ethynylcytidine (Taiho) |
| Topoisomerase inhibitors | Amsacrine | Rubitecan (SuperGen) |
| | Epirubicin | Exatecan mesylate (Daiichi) |
| | Etoposide | Quinamed (ChemGenex) |
| | Teniposide or mitoxantrone | Gimatecan (Sigma-Tau) |
| | Irinotecan (CPT-11) | Diflomotecan (Beaufour-Ipsen) |
| | 7-Ethyl-10-hydroxycamptothecin | TAS-103 (Taiho) |
| | Topotecan | Elsamitrucin (Spectrum) |
| | Dexrazoxanet (TopoTarget) | J-107088 (Merck & Co) BNP-1350 (BioNumerik) |
| | Pixantrone (Novuspharma) | CKD-602 (Chong Kun Dang) |
| | Rebeccamycin analogue (Exelixis) | KW-2170 (Kyowa Hakko) |
| | BBR-3576 (Novuspharma) | |
| Antitumour antibiotics | Dactinomycin (Actinomycin D) | Amonafide Azonafide |
| | Doxorubicin (Adriamycin) | Anthrapyrazole |
| | Deoxyrubicin | Oxantrazole |
| | Valrubicin | Losoxantrone |
| | Daunorubicin (Daunomycin) | Bleomycin sulfate (Blenoxan) |
| | Epirubicin | Bleomycinic acid |
| | Therarubicin | Bleomycin A |
| | Idarubicin | Bleomycin B |
| | Rubidazon | Mitomycin C |
| | Plicamycinp | MEN-10755 (Menarini) |
| | Porfiromycin | GPX-100 (Gem Pharmaceuticals) |
| | Cyanomorpholinodoxorubicin | |
| | Mitoxantron (Novantron) | |
| Antimitotic agents | Paclitaxel | SB 408075 |
| | Docetaxel | (GlaxoSmithKline) |
| | Colchicine | E7010 (Abbott) |

TABLE 1-continued

| | | |
|---|---|---|
| | Vinblastine | PG-TXL (Cell Therapeutics) |
| | Vincristine | IDN 5109 (Bayer) |
| | Vinorelbine | A 105972 (Abbott) |
| | Vindesine | A 204197 (Abbott) |
| | Dolastatin 10 (NCI) | LU 223651 (BASF) |
| | Rhizoxin (Fujisawa) | D 24851 (ASTA Medica) |
| | Mivobulin (Warner-Lambert) | ER-86526 (Eisai) |
| | Cemadotin (BASF) | Combretastatin A4 (BMS) |
| | RPR 109881A (Aventis) | Isohomohalichondrin-B (PharmaMar) |
| | TXD 258 (Aventis) | ZD 6126 (AstraZeneca) |
| | Epothilone B (Novartis) | PEG-Paclitaxel (Enzon) |
| | T 900607 (Tularik) | AZ10992 (Asahi) |
| | T 138067 (Tularik) | !DN-5109 (Indena) |
| | Cryptophycin 52 (Eli Lilly) | AVLB (Prescient NeuroPharma) |
| | Vinflunine (Fabre) | Azaepothilon B (BMS) |
| | Auristatin PE (Teikoku Hormone) | BNP-7787 (BioNumerik) |
| | BMS 247550 (BMS) | CA-4-prodrugs (OXiGENE) |
| | BMS 184476 (BMS) | Dolastatin-10 (NrH) |
| | BMS 188797 (BMS) | CA-4 (OXiGENE) |
| | Taxoprexin (Protarga) | |
| Aromatase inhibitors | Aminoglutethimide | Exemestan |
| | Letrozole | Atamestan (BioMedicines) |
| | Anastrazole | YM-511 (Yamanouchi) |
| | Formestan | |
| Thymidylate synthase inhibitors | Pemetrexed (Eli Lilly) | Nolatrexed (Eximias) |
| | ZD-9331 (BTG) | CoFactor ™ (BioKeys) |
| DNA antagonists | Trabectedin (PharmaMar) | Mafosfamide (Baxter International) |
| | Glufosfamide (Baxter International) | Apaziquone (Spectrum Pharmaceuticals) |
| | Albumin + 32P (Isotope Solutions) | O6-benzylguanine (Paligent) |
| | Thymectacin (NewBiotics) | |
| | Edotreotid (Novartis) | |
| Farnesyl transferase inhibitors | Arglabin (NuOncology Labs) | Tipifarnib (Johnson & Johnson) |
| | Ionafarnib (Schering-Plough) | Perillyl alcohol (DOR BioPharma) |
| | BAY-43-9006 (Bayer) | |
| Pump inhibitors | CBT-1 (CBA Pharma) | Zosuquidar trihydrochloride (Eli Lilly) |
| | Tariquidar (Xenova) | Biricodar dicitrate (Vertex) |
| | MS-209 (Schering AG) | |
| Histone acetyl transferase inhibitors | Tacedinaline (Pfizer) | Pivaloyloxymethyl butyrate (Titan) |
| | SAHA (Aton Pharma) | Depsipeptide (Fujisawa) |
| | MS-275 (Schering AG) | |
| Metalloproteinase inhibitors | Neovastat (Aeterna Laboratories) | CMT-3 (CollaGenex) |
| | Marimastat (British Biotech) | BMS-275291 (Celltech) |
| Ribonucleoside reductase inhibitors | Gallium maltolate (Titan) | Tezacitabine (Aventis) |
| | Triapin (Vion) | Didox (Molecules for Health) |
| TNF-alpha agonists/antagonists | Virulizin (Lorus Therapeutics) | Revimid (Celgene) |
| | CDC-394 (Celgene) | |
| Endothelin-A receptor antagonists | Atrasentan (Abbot) | YM-598 (Yamanouchi) |
| | ZD-4054 (AstraZeneca) | |
| Retinoic acid receptor agonists | Fenretinide (Johnson & Johnson) | Alitretinoin (Ligand) |
| | LGD-1550 (Ligand) | |
| Immunomodulators | Interferon | Dexosome therapy (Anosys) |
| | Oncophage (Antigenics) | Pentrix (Australian Cancer Technology) |
| | GMK (Progenics) | JSF-154 (Tragen) |
| | Adenocarcinoma vaccine (Biomira) | Cancer vaccine (Intercell) |
| | CTP-37 (AVI BioPharma) | Norelin (Biostar) |
| | JRX-2 (Immuno-Rx) | BLP-25 (Biomira) |
| | PEP-005 (Peplin Biotech) | MGV (Progenics) |
| | Synchrovax vaccine (CTL Immuno) | β-Alethin (Dovetail) |
| | Melanoma vaccine (CTL Immuno) | CLL-Thera (Vasogen) |
| | p21-RAS vaccine (GemVax) | |
| Hormonal and antihormonal agents | Ooestrogens | Prednisone |
| | Conjugated ooestrogens | Methylprednisolone |
| | Ethynyloestradiol | Prednisolone |
| | Chlorotrianisene | Aminoglutethimide |
| | Idenestrol | Leuprolide |

TABLE 1-continued

| | | |
|---|---|---|
| | Hydroxyprogesterone caproate | Goserelin |
| | Medroxyprogesterone | Leuporelin |
| | Testosterone | Centrorelix |
| | Testosterone propionate | Bicalutamide |
| | Fluoxymesterone | Flutamide |
| | Methyltestosterone | Octreotide |
| | Diethylstilbestrol | Nilutamide |
| | Megestrol | Mitotan |
| | Tamoxifen | P-04 (Novogen) |
| | Toremofin | 2-Methoxyoestradiol (EntreMed) |
| | Dexamethasone | Arzoxifen (Eli Lilly) |
| Photodynamic agents | Talaporfin (Light Sciences) | Pd-Bacteriopheophorbid (Yeda) |
| | Theralux (Theratechnologies) | Lutetium-Texaphyrin (Pharmacyclics) |
| | Motexafin-Gadolinium (Pharmacyclics) | Hypericin |
| Tyrosine kinase inhibitors | Imatinib (Novartis) | Kahalide F (PharmaMar) |
| | Leflunomide (Sugen/Pharmacia) | CEP-701 (Cephalon) |
| | | CEP-751 (Cephalon) |
| | ZD1839 (AstraZeneca) | MLN518 (Millenium) |
| | Erlotinib (Oncogene Science) | PKC412 (Novartis) |
| | | Phenoxodiol O |
| | Canertjnib (Pfizer) | Trastuzumab (Genentech) |
| | Squalamine (Genaera) | C225 (ImClone) |
| | SU5416 (Pharmacia) | rhu-Mab (Genentech) |
| | SU6668 (Pharmacia) | MDX-H210 (Medarex) |
| | ZD4190 (AstraZeneca) | 2C4 (Genentech) |
| | ZD6474 (AstraZeneca) | MDX-447 (Medarex) |
| | Vatalanib (Novartis) | ABX-EGF (Abgenix) |
| | PKI166 (Novartis) | IMC-1C11 (ImClone) |
| | GW2016 (GlaxoSmithKline) | |
| | EKB-509 (Wyeth) | |
| | EKB-569 (Wyeth) | |
| Various agents | SR-27897 (CCK-A inhibitor, Sanofi-Synthelabo) | BCX-1777 (PNP inhibitor, BioCryst) |
| | Tocladesine (cyclic AMP agonist, Ribapharm) | Ranpirnase (ribonuclease stimulant, Alfacell) |
| | Alvocidib (CDK inhibitor, Aventis) | Galarubicin (RNA synthesis inhibitor, Dong-A) |
| | CV-247 (COX-2 inhibitor, Ivy Medical) | Tirapazamine (reducing agent, SRI International) |
| | P54 (COX-2 inhibitor, Phytopharm) | N-Acetylcysteine (reducing agent, Zambon) |
| | CapCell ™ (CYP450 stimulant, Bavarian Nordic) | |
| | GCS-IOO (gal3 antagonist, GlycoGenesys) | R-Flurbiprofen (NF-kappaB inhibitor, Encore) |
| | G17DT immunogen (gastrin inhibitor, Aphton) | 3CPA (NF-kappaB inhibitor, Active Biotech) |
| | Efaproxiral (oxygenator, Allos Therapeutics) | Seocalcitol (vitamin D receptor agonist, Leo) |
| | PI-88 (heparanase inhibitor, Progen) | 131-I-TM-601 (DNA antagonist, TransMolecular) |
| | Tesmilifen (histamine antagonist, YM BioSciences) | Eflornithin (ODC inhibitor, ILEX Oncology) |
| | Histamine (histamine H2 receptor agonist, Maxim) | Minodronic acid (osteoclast inhibitor, Yamanouchi) |
| | Tiazofurin (IMPDH inhibitor, Ribapharm) | Indisulam (p53 stimulant, Eisai) |
| | Cilengitide (integrin antagonist, Merck KGaA) | Aplidin (PPT inhibitor, PharmaMar) |
| | SR-31747 (IL-1 antagonist, Sanofi-Synthelabo) | Rituximab (CD20 antibody, Genentech) |
| | CCI-779 (mTOR kinase inhibitor, Wyeth) | Gemtuzumab (CD33 antibody, Wyeth Ayerst) |
| | Exisulind (PDE-V inhibitor, Cell Pathways) | PG2 (haematopoiesis promoter, Pharmagenesis) |
| | CP-461 (PDE-V inhibitor, Cell Pathways) | Immunol ™ (triclosan mouthwash, Endo) |
| | AG-2037 (GART inhibitor, Pfizer) | Triacetyluridine (uridine prodrug, Wellstat) |
| | WX-UK1 (plasminogen activator | SN-4071 (sarcoma agent, Signature BioScience) |

TABLE 1-continued

| | |
|---|---|
| inhibitor, Wilex) | TransMID-107 ™ |
| PBI-1402 (PMN stimulant, ProMetic LifeSciences) | (immunotoxin, KS Biomedix) |
| Bortezomib (proteasome inhibitor, Millennium) | PCK-3145 (apoptosis promoter, Procyon) |
| SRL-172 (T-cell stimulant, SR Pharma) | Doranidazole (apoptosis promoter, Pola) |
| TLK-286 (glutathione-S transferase inhibitor, Telik) | CHS-828 (cytotoxic agent, Leo) trans-Retinic acid |
| PT-100 (growth factor agonist, Point Therapeutics) | (differentiator, NIH) MX6 (apoptosis promoter, MAXIA) |
| Midostaurin (PKC inhibitor, Novartis) | Apomine (apoptosis promoter, ILEX Oncology) |
| Bryostatin-1 (PKC stimulant, GPC Biotech) | Urocidin (apoptosis promoter, Bioniche) |
| CDA-II (apoptosis promoter, Everlife) | Ro-31-7453 (apoptosis promoter, La Roche) |
| SDX-101 (apoptosis promoter, Salmedix) | Brostallicin (apoptosis promoter, Pharmacia) |
| Ceflatonin (apoptosis promoter, ChemGenex) | |

In a preferred embodiment, a compound of the invention is administered in combination with one or more known anti-tumour agents, such as the following: oestrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors, angiogenesis inhibitors.

The compounds of the invention are suitable, in particular, for administration in combination with radiotherapy. The synergistic effects of VEGF inhibition in combination with radiotherapy are known to the person skilled in thye art (WO 00/61186).

The expression "oestrogen receptor modulators" in the course of the present invention refers to compounds which interfere with or inhibit the binding of oestrogen to the oestrogen receptor, irrespective of how this occurs. The oestrogen receptor modulators include, for example, tamoxifen, raloxifen, idoxifen, LY353381, LY 117081, toremifen, fulvestrant, 4-[7-(2,2-Dimethyl-1-oxopropoxy-4-methyl-2-[4-[2-(1-piperidinyl)ethoxy]phenyl]-2H-1-benzopyran-3-yl]phenyl 2,2-dimethylpropanoate, 4,4'-dihydroxy-benzophenon-2,4-dinitrophenylhydrazone and SH646, but this is not intended to represent a restriction.

The expression "androgen receptor modulators" in the course of the present invention refers to compounds which interfere with or inhibit the binding of androgens to the androgen receptor, irrespective of how this occurs. The androgen receptor modulators include, for example, finasteride and other 5alpha-reductase inhibitors, nilutamide, flutamide, bicalutamide, liarozole and abirateron acetate, but this is not intended to represent a restriction.

The expression "retinoid receptor modulators" in the course of the present invention refers to compounds which interfere with or inhibit the binding of retinoids to the retinoid receptor, irrespective of how this occurs. The retinoid receptor modulators include, for example, bexaroten, tretinoin, 13-cis-retinoic acid, 9-cis-retinoic acid, alpha-difluoromethylornithine, ILX23-7553, trans-N-(4'-hydroxyphenyl) retinamide and N-4-carboxyphenylretinamide, but this is not intended to represent a restriction.

The expression "cytotoxic agents" in the course of the present invention refers to compounds which primarily trigger cell death through direct action on cell function(s) or which interfere with or inhibit cell myosis, such as alkylating agents, tumour necrosis factors, intercalating agents, microtubule inhibitors and topoisomerase inhibitors. The cytotoxic agents include, for example, tirapazimin, sertenef, cachectine, ifosfamide, tasonermine, lonidamine, carboplatin, altretamine, prednimustine, dibromodulcit, ranimustine, fotemustine, nedaplatin, oxaliplatin, temozolomide, heptaplatin, estramustin, improsulfan-tosylate, trofosfamide, nimustine, dibrospidium chloride, pumitepa, lobaplatin, satraplatin, profiromycin, cisplatin, irofulven, dexifosfamide, cis-aminodichloro(2-methylpyridine)platinum, benzylguanine, glufosfamide, GPX100, (trans,trans,trans)-bis-mu-(hexane-1,6-diamine)-mu-[diamine-platinum(II)]bis-[diamine(chloro) platinum(II)]tetrachloride, diarizidinylspermine, arsenium trioxide, 1-(11-dodecylamino-10-hydroxy-undecyl)-3,7-dimethylxanthine, zorubicin, idarubicin, daunorubicin, bisantren, mitoxantron, pirarubicin, pinafide, valrubicine, amrubicin, antineoplaston, 3'-desamino-3'-morpholino-13-desoxo-10-hydroxycaminomycin, annamycin, galarubicin, elinafide, MEN10755 and 4-desmethoxy-3-desamino-3-aziridinyl-4-methylsulfonyldaunorubicin (WO 00/50032), but this is not intended to represent a restriction.

The microtubule inhibitors include, for example, paclitaxel, vindesine sulfate, 3',4'-dideshydro-4'-desoxy-8'-norvincaleukoblastine, docetaxol, rhizoxine, dolastatin, mivobuline isethionate, auristatin, cemadotine, RPR109881, BMS184476, vinflunine, cryptophycine, 2,3,4,5,6-pentafluoro-N-(3-fluoro-4-methoxyphenyl)-benzenesulfonamide, anhydrovinblastine, N,N-dimethyl-L-valyl-L-valyl-N-methyl-L-valyl-L-prolyl-L-proline-t-butylamide, TDX258 and BMS188797, but this is not intended to represent a restriction.

The topoisomerase inhibitors include, for example, topotecane, hycaptamine, irinotecane, rubitecane, 6-ethoxypropionyl-3',4'-O-exo-benzylidene-chartreusine, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo-[de]-pyrano-[3',4':b,7]indolizino[1,2b]quiinoline-10,13(9H,15H)-dione, lurtotecane, 7-[2-(N-isopropylamino)ethyl]-(20S)-camptothecine, BNP1350, BNPI1100, BN80915, BN80942, etoposide phosphate, teniposide, sobuzoxane, 2'-dimethylamino-2'-desoxyetoposide, GL331, N-[2-(dimethylamino) ethyl]-9-hydroxy-5,6-dimethyl-6H-pyrido[4,3-b]carbazole- 1-carboxamide, asulacrine, (5a,5aB,8aa,9b)-9-[2-[N-[2-(dimethylamino)ethyl]-N-methylamino]ethyl]-5-[4-hydroxy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxy-benzo[c]phenanthridinium, 6,9-bis[(2-aminoethyl)amino]-benzo[g]isoquinoline-5,10-dione, 5-(3-aminopropylamino)-7,10-dihydroxy-2-(2-hydroxyethylaminomethyl)-6H-pyrazolo[4,5,1-de]acridine-6-one, N-[1-[2(diethylamino)ethylamino]-7-methoxy-9-oxo-9H-thioxanthen-4-ylmethyl]formamide, N-(2-(dimethyl-amino)-ethyl)acridine-4-carboxamide, 6-[[2-(dimethylamino)ethyl]amino]-3-hydroxy-7H-indeno[2,1-c]quinolin-7-one and dimesna, but this is not intended to represent a restriction.

The antiproliferative agents include, for example, antisense RNA- and antisense-DNA oligonucleotides, such as G3139, ODN698, RVASKRAS, GEM231 and INX3001, as well as antimetabolites, such as enocitabine, carmofur, tegafur, pentostatine, doxifluridine, trimetrexate, fludarabine, capecitabine, galocitabine, cytarabin-ocfosfate, fosteabine sodiumhydrate, raltitrexed, paltitrexide, emitefur, tiazofurine, decitabine, nolatrexed, pemetrexed, nelzarabine, 2'-desoxy-2'-methylidenecytidine, 2'-fluoromethylene-2'-desoxycytidine, N-[5-(2,3-dihydrobenzofuryl)sulfonyl]-N'-(3,4-dichlorophenyl)urea, N6-[4-desoxy-4-[N2-[2(E),4(E)-tetradecadienoyl]glycylamino]-L-glycero-B-L-mannoheptopyranosyl]adenine, aplidine, ecteinascidine, troxacitabine, 4-[2-amino-4-oxo-4,6,7,8-tetrahydro-3H-pyrimidino[5,4-b]-1,4-thiazine-6-yl-(S)-ethyl]-2,5-thienoyl-L-glutaminic acid, aminopterine, 5-fluorouracil, alanosine, 11-acetyl-8-(carbamoyloxymethyl)-4-formyl-6-methoxy-14-oxa-1,11-diazatetracyclo-(7.4.1.0.0)-tetradeca-2,4,6-trien-9-yl-acetic acid ester, swainsonine, lometrexole, dexrazoxane, methioninase, 2'-cyano-2'-desoxy-N4-palmitoyl-1-B-D-arabinofuranosylcytosine and 3-aminopyridine-2-carboxaldehyde thiosemicarbazone, but this is not intended to represent a restriction.

The "antiproliferative agents" also include monoclonal antibodies against growth factors which have not been listed under "angiogenesis inhibitors", such as trastuzumab, as well as tumour suppressor genes, such as p53.

In a further aspect of the invention, a medicament in accordance with the above aspects and embodiments is provided, where a medicament of this type comprises at least one additional pharmacologically active substance (drug, ingredient).

In a preferred embodiment, the at least one additional pharmacologically active substance is a substance as described here.

In a further aspect of the invention, a medicament in accordance with the above aspects and embodiments is provided, where the medicament is administered before and/or during and/or after the treatment with at least one additional pharmacologically active substance.

In a preferred embodiment, the at least one additional pharmacologically active substance is a substance as described here.

In a further aspect of the invention, a pharmaceutical composition comprising a therapeutically effective amount of at least one compound of the invention is provided.

In a preferred embodiment, the pharmaceutical composition comprises at least one additional compound selected from the group consisting of physiologically tolerated excipients and adjuvants and/or additional pharmaceutically active substance apart from the compounds of the invention.

In a further aspect of the invention, a pharmaceutical composition is disclosed which comprises at least one compound of the invention, at least one pharmacologically active substance apart from the compounds of the invention as described here, and a physiologically tolerated excipient and/or adjuvant.

A further embodiment of the present invention is a process for the preparation of the pharmaceutical compositions, characterised in that one or more compounds according to the invention and one or more compounds selected from the group consisting of solid, liquid or semi-liquid extenders, adjuvants, additives, diluents, excipients and pharmacologically active substances apart from the compounds according to the invention are converted in a suitable administration form.

In a further aspect of the invention, a kit is provided comprising a therapeutically effective amount of at least one compound of the invention and/or at least one pharmaceutical composition as described here and a therapeutically effective amount of at least one further pharmacologically active substance apart from the compounds of the invention.

The pharmaceutical compositions of the present invention can be administered in any manner by means of which the intended purpose is achieved. For example, administration may be by oral, parenteral, topical, enteral, intravenous, intramuscular, inhalant, nasal, intraarticular, intraspinal, transtracheal, transocular, subcutaneous, intraperitoneal, trans-dermal or buccal routes. Alternatively or simultaneously, administration may be by oral routes. The dose administered depends on the age, state of health and weight of the recipient, type of any simultaneous treatment, frequency of treatment, and type of effect desired. Parenteral administration is preferred. Oral administration is particularly preferred.

Suitable dosage forms include, but are not limited to, capsules, tablets, pellets, dragees, semi-solid substances, powders, granules, suppositories, ointments, creams, lotions, inhalants, injections, cataplasms, gels, tape, eye drops, solution, syrups, aerosols, suspension, emulsion, which can be prepared by methods known in the prior art, for example as described below:

tablets: mixing of active compound(s) and adjuvants, compression of the mixture to give tablets (direct compression), optionally granulation of part of the mixture before compression.

capsules: mixing of compound(s) and adjuvants to give a flowable powder, optionally granulation of the powder, introduction of powders/granules into opened capsules, sealing of the capsules.

semi-solid substances (ointments, gels, creams): dissolution/dispersion of the active compound(s) in an aqueous or fatty excipient; subsequent mixing of the water/fat phase with corresponding fat/water phase, homogenisation (creams only).

suppositories (rectal and vaginal): dissolution/dispersion of the active compound(s) in excipient material liquefied by heat (rectal: excipient material normally a wax; vaginal: excipient normally a heated solution of a gelling agent), pouring of the mixture into suppository moulds, solidification and removal of suppositories from the moulds.

aerosols: dissolution/dispersion of the active agent(s) in a propellant gas, transfer of the mixture into an atomiser.

In general, non-chemical methods for the preparation of pharmaceutical compositions and/or pharmaceutical preparations comprise processing steps in suitable mechanical means known in the prior art which convert one or more compounds of the invention into an administration form which is suitable for administration to a patient in need of such a treatment. The conversion of one or more compounds of the invention into such an administration form usually comprises the addition of one or more compounds, selected from the group consisting of excipients, extenders, adjuvants and pharmaceutical active compounds apart from the compounds of the invention. Suitable method steps are, but are not restricted to, combining, milling, mixing, granulating, dissolving, dispersing, homogenising, casting and/or compressing the respective active and non-active ingredients. Mechanical means for carrying out the said processing steps are known in the prior art, for example from Ullmann's Encyclopedia of Industrial Chemistry, 5th Edition. Active compounds here are preferably at least one compound of the invention and one or more additional compounds apart from the compounds of the invention which have valuable pharmaceutical properties, preferably those pharmaceutical active agents apart from the compounds of the invention which are disclosed here.

Particularly suitable for oral use are tablets, pills, dragees, capsules, powders, granules, syrups, juices or drops, suitable for rectal use are suppositories, suitable for parenteral use are solutions, preferably oil-based or aqueous solutions, furthermore suspensions, emulsions or implants, and suitable for topical use are ointments, creams or powders. The compounds of the invention may also be lyophilised and the resultant lyophilisates used, for example, for the preparation of injection preparations. The preparations indicated may be sterilised and/or comprise adjuvants, such as lubricants, preservatives, stabilisers and/or wetting agents, emulsifiers, salts for modifying the osmotic pressure, buffer substances, dyes, flavours and/or a plurality of further active compounds, for example one or more vitamins.

Suitable extenders are organic or inorganic substances which are suitable for enteral (for example oral), parenteral or topical administration and do not react with the compounds of the invention, for example water, vegetable oils, benzyl alcohols, alkylene glycols, polyethylene glycols, glycerol triacetate, gelatin, carbohydrates, such as lactose, sucrose, mannitol, sorbitol or starch (maize starch, wheat starch, rice starch, potato starch), cellulose preparations and/or calcium phosphates, for example tricalcium phosphate or calcium hydrogen phosphate, magnesium stearate, talc, gelatin, tragacanth, methyl cellulose, hydroxypropylmethylcellulose, sodium carboxymethylcellulose, polyvinylpyrrolidone and/or Vaseline.

If desired, it is possible to add disintegrants, such as the above-mentioned starches and also carboxymethylstarch, crosslinked polyvinylpyrrolidone, agar, or alginic acid or a salt thereof, such as sodium alginate. Adjuvants include, without limitation, flow regulators and lubricants, for example silicic acid, talc, stearic acid or salts thereof, such as magnesium stearate or calcium stearate, and/or polyethylene glycol. Dragee cores are provided with suitable coatings, which, if desired, are resistant to gastric juices. For this purpose, concentrated saccharide solutions may be used, which may optionally contain gum arabic, talc, polyvinylpyrrolidone, polyethylene glycol and/or titanium dioxide, lacquer solutions and suitable organic solvents or solvent mixtures. In order to produce coatings which are resistant to gastric juices or to provide an administration form having the advantage of extended action, the tablet, dragee or pill may comprise an inner and outer dosage component, the latter being in the form of a sheath around the former. The two components can be separated by a layer which is resistant to gastric juices, which counters disintegration in the stomach and allows the inner component to pass intact into the duodenum or to be delayed in release. A variety of materials can be used for such layers or coatings which are resistant to gastric juices, where such materials include a number of polymeric acids and mixtures of polymeric acids with materials such as shellac, acetyl alcohol, solutions of suitable cellulose preparations, such as acetylcellulose phthalate, cellulose acetate or hydroxypropylmethylcellulose phthalate, are used. Dyes or pigments may be added to the tablets or dragee coatings, for example for identification or in order to label combinations of active compound doses.

Suitable excipient substances are organic or inorganic substances which are suitable for enteral (e.g. oral) or parenteral administration or topical application and do not react with the novel compounds, for example water, vegetable oils, benzyl alcohols, polyethylene glycols, gelatin, carbohydrates, such as lactose or starch, magnesium stearate, talc and petroleum jelly. In particular, tablets, dragees, capsules, syrups, suspensions, drops or suppositories are used for enteral administration, solutions, preferably oily or aqueous solutions, furthermore suspensions, emulsions or implants are used for parenteral administration, and ointments, creams or powders are used for topical application. The compounds of the invention can also be lyophilised and the lyophilisates obtained can be used, for example, for the preparation of injection preparations.

The preparations indicated can be sterilised and/or can contain extenders, such as lubricants, preservatives, stabilisers and/or wetting agents, emulsifiers, salts for modifying the osmotic pressure, buffer substances, colorants, flavourings and/or aromatisers. They may optionally also comprise one or more further active compounds, for example one or more vitamins.

Further pharmaceutical preparations which can be used orally are, inter alia, push-fit gelatin capsules, and soft, sealed capsules made of gelatin and a plasticiser, such as glycerol or sorbitol. The push-fit capsules can contain the active compounds in the form of granules, which may be mixed with fillers, such as lactose, binders, such as starches, and/or lubricants, such as talc or magnesium stearate, and optionally stabilisers. In soft capsules, the active compounds are preferably dissolved or suspended in suitable liquids, such as fatty oils or liquid paraffin. In addition, stabilisers may be added.

The liquid forms into which the novel compositions of the present invention may be incorporated for oral administration include aqueous solutions, suitably flavoured syrups, aqueous or oil suspensions and flavoured emulsions with edible oils, such as cottonseed oil, sesame oil, coconut oil or peanut oil, as well as elixirs and similar pharmaceutical vehicles. Suitable dispersants or suspension agents for aqueous suspensions include synthetic and natural gums, such as tragacanth, gum arabic, alginate, dextran, sodium carboxymethylcellulose, methylcellulose, polyvinylpyrrolidone or gelatin.

The suitable formulations for parenteral administration include aqueous solutions of the active compounds in water-soluble form, for example, water-soluble salts and alkaline solutions. In addition, suspensions of the active compounds can be administered as suitable oily injection suspensions. Suitable lipophilic solvents or vehicles include fatty oils, for example sesame oil, or synthetic fatty acid esters, for example ethyl oleate or triglycerides or polyethylene glycol 400 (the compounds are soluble in PEG 400).

Aqueous injection suspensions may comprise substances which increase the viscosity of the suspension, including, for example, sodium carboxymethylcellulose, sorbitol and/or dextran, the suspension may optionally also comprise stabilisers.

For administration as inhalation spray, it is possible to use sprays in which the active compound is either dissolved or suspended in a propellant gas or propellant gas mixture (for example $CO_2$ or chlorofluorocarbons). The active compound is preferably used here in micronised form, where one or more additional physiologically acceptable solvents may be present, for example ethanol. Inhalation solutions can be administered with the aid of conventional inhalers.

The possible pharmaceutical preparations which can be used rectally include, for example, suppositories, which consist of a combination of one or more of the active compounds with a suppository base. Suitable suppository bases are, for example, natural or synthetic triglycerides or paraffin hydrocarbons. In addition, it is also possible to use gelatin rectal capsules, which consist of a combination of the active compounds with a base. Possible base materials include, for example, liquid triglycerides, polyethylene glycols or paraffin hydrocarbons.

For medicinal use, the compounds of the present invention are in the form of pharmaceutically acceptable salts. However, other salts may be useful in the preparation of the compounds of the invention or of pharmaceutically acceptable salts thereof. Suitable pharmaceutically acceptable salts of the compounds of this invention include acid-addition salts, which can be formed, for example by mixing a solution of the compound according to the invention with a solution of a pharmaceutically acceptable acid, such as hydrochloric acid, sulfuric acid, methanesulfonic acid, fumaric acid, maleic acid, succinic acid, acetic acid, benzoic acid, oxalic acid, citric acid, tartaric acid, carbonic acid or phosphoric acid. If the compounds of the invention carry an acidic moiety, suitable pharmaceutically acceptable salts thereof may furthermore include alkali-metal salts, for example sodium or potassium salts; alkaline-earth metal salts, for example calcium or magnesium salts; and salts formed with suitable organic bases, for example quaternary ammonium salts.

The pharmaceutical preparations can be employed as medicaments in human and veterinary medicine. As used here, the expression "effective amount" means the amount of a medicament or pharmaceutical agent which causes the biological or medical response sought, for example, by a researcher or clinician in a tissue, system, animal or human. In addition, the expression "therapeutically effective amount" means any amount which, compared with a corresponding subject who has not received such an amount, results in improved treatment, healing, prevention or amelioration of a disease, disorder, or side effect, or in a decrease in the rate of advancement of a disease or disorder. The expression also includes within its scope amounts which cause an increase in normal physiological function. The therapeutically effective amount of one or more compounds of the invention is known to the person skilled in the art or can be easily determined by standard methods known in the art.

The compounds of the invention and the additional active substances are generally administered analogously to commercially available preparations. Suitable doses which are therapeutically effective are usually in the range between 0.0005 mg and 1000 mg, preferably between 0.005 mg and 500 mg and in particular between 0.5 mg and 100 mg per dosage unit. The daily dose is preferably between about 0.001 mg/kg and 10 mg/kg of body weight.

It will be clear to the person skilled in the art that dosage amounts can vary depending on the specific compound, the severity of the symptoms and the sensitivity of the subject to side effects. Some of the specific compounds have a stronger effect than others. The person skilled in the art can easily determine preferred dosages for a given compound in various ways. A preferred way is to measure the physiological potency of a given compound.

For the purpose of the present invention, all mammalian species are regarded as included. In a preferred embodiment, such mammals are selected from the group consisting of "primates, humans, rodents, horses, cattle, dog breeds, cats, domesticated animals, breeding cattle, livestock, pets, cow, sheep, pig, goat, horse, pony, donkey, hinny, mule, hare, rabbit, cat, dog, guinea pig, hamster, rat, mouse". These mammals are particularly preferably humans. Animal models are of interest for experimental investigations and offer a model for the treatment of human diseases.

The specific dose for the individual patient depends, however, on the multitude of factors, for example on the efficacy of the specific compounds employed, on the age, body weight, general state of health, gender, on the diet, on the time and method of administration, on the excretion rate, the type of administration and the administration form to be administered, the pharmaceutical combination and severity of the particular disorder to which the therapy applies. The respective therapeutically effective dose for the particular patient can easily be determined by routine experiments, for example by the doctor who advises on or attends this therapeutic treatment.

In the case of many disorders, the sensitivity of a particular cell to treatment with the compounds in question can be determined by in-vitro tests. Typically, a culture of the cell is combined with the compound in question in various concentrations for a period of time which enables the active agents to exhibit a relevant reaction, usually between one hour and one week. For in-vitro tests, cultured cells from a biopsy sample can be used.

In a further aspect of the invention, intermediate compound of the formula (V) are provided,

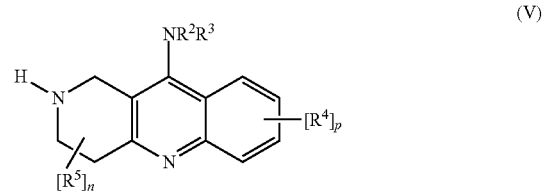

in which $R^2$, $R^3$, $R^4$, $R^5$, n and p have the indicated meanings defined here.

In a further aspect of the invention, intermediate compound of the formula (II) are provided,

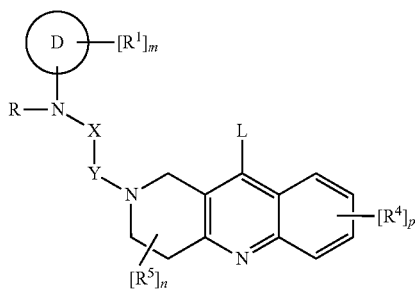

in which D, X, Y, R, $R^1$, $R^4$, $R^5$, m, n and p have the indicated meanings defined here and L is a halogen, tosylate, mesylate or triflate.

Even without further comments, it is assumed that a person skilled in the art will be able to utilise the above description in the broadest scope. The preferred embodiments should therefore merely be regarded as descriptive disclosure which is absolutely not limiting in any way.

Above and below, all temperatures are indicated in ° C. In the following examples, "conventional work-up" means that, if necessary, the solvent is removed, water is added if necessary, the pH is adjusted, if necessary, to between 2 and 10, depending on the constitution of the end product, the mixture is extracted with ethyl acetate or dichloromethane, the phases are separated, the organic phase is washed with saturated $NaHCO_3$ solution, if desired with water and saturated NaCl solution, dried over sodium sulfate, filtered and evaporated, and the product is purified by chromatography on silica gel, by preparative HPLC and/or by crystallisation. The purified compounds are, if desired, freeze-dried.

List of Abbreviations and Acronyms:

AcOH acetic acid, anh anhydrous, atm atmosphere(s), BOC tert-butoxycarbonyl CDI 1,1'-carbonyldiimidazole, conc. concentrated, d day(s), decomp. decomposition, DMAC N,N-dimethylacetamide, DMPU 1,3-dimethyl-3,4,5,6-tetrahydro-2(1H)-pyrimidinone, DMF N,N-dimethylformamide, DMSO dimethyl sulfoxide, DPPA diphenylphosphoryl azide, EDCl 1-(3-dimethylaminopropyl)-3-ethylcarbodiimide, EtOAc ethyl acetate, EtOH ethanol (100%), $Et_2O$ diethyl ether, $Et_3N$ triethylamine, h hour(s), MeOH methanol, pet. ether petroleum ether (boiling range 30-60° C.), temp. temperature, THF tetrahydrofuran, TFA trifluoro-AcOH, Tf trifluoromethanesulfonyl.

The contents of all cited references are hereby incorporated in their entirety by way of reference. The invention is explained in greater detail by the following examples, but without being restricted thereto.

EXAMPLES

I. Synthesis of Selected Compounds of the Invention

The following compounds were synthesised and characterised. However, part of the general knowledge of the person skilled in the art is to prepare and characterise these compounds by other methods.

Example 1

Synthesis of N-(5-chloro-2-methoxyphenyl)-2-[10-(2-oxo-2-pyrrolidin-1-yl-ethylamine)-3,4-dihydro-1H-benzo[b]-1,6-naphthyridin-2-yl]acetamide (3)

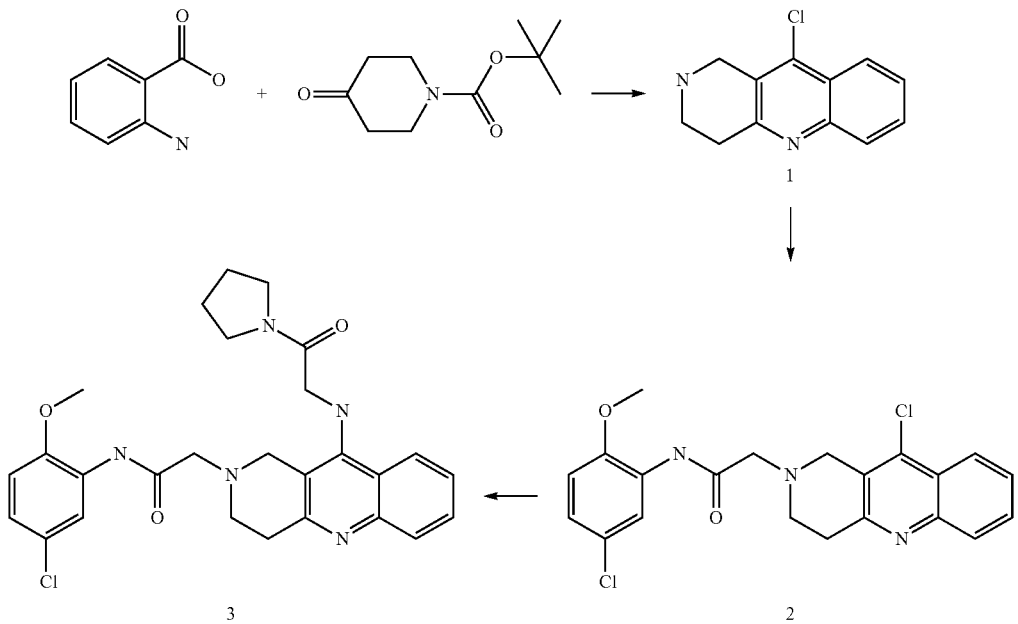

a. 2.00 g (14.6 mmol) of anthranilic acid and 2.90 g (14.6 mmol) of tert-butyl 4-oxopiperidine-1-carboxylate are dissolved in 50 ml of phosphoryl chloride and stirred at room temperature for 2 hours. The solution is then cooled in an ice bath and adjusted to pH=8 using 1N $NaHCO_3$ solution. This solution was then extracted 2× with 100 ml of dichloromethane each time. The organic phase was dried over magnesium sulfate, filtered off and evaporated to dryness in vacuo, giving 2.9 g (76.4%) of 1 as yellowish crystalline residue.

b. 1.54 g (7.04 mmol) of 1, 2.00 g (7.2 mmol) of 2-bromo-N-(5-chloro-2-methoxyphenyl)acetamide and 4.68 g (14.4 mmol) of caesium carbonate are stirred in 50 ml of DMF for 24 hours at room temperature and for 2 hours at 50° C. 100 ml of water are then added to the reaction mixture, and the solid material is filtered off, giving 2.34 g (79.8%) of 2 as amorphous solid product.

c. 0.30 g (0.72 mmol) of 2, 0.18 g (1.1 mmol) of 2-amino-1pyrrolidin-1-yl-ethanone×HCl, 0.2 g (2.1 mmol) of phenol and 0.15 ml (1.1 mmol) of triethylamine are stirred at 120° C. for 6 hours. The reaction mixture is then taken up in 50 ml of ethyl acetate and 50 ml of 1N NaOH solution. After extraction by shaking, the organic phase is separated off and extracted a further 2× with 30 ml of saturated NaCl solution each time. It is then evaporated to dryness in vacuo. The residue is taken up in a little methanol, and 5 ml of 6N HCl in isopropanol are added. The mixture is then again evaporated to dryness in vacuo. A little ethanol is added to the residue, and the precipitate is filtered off, giving 98 mg (25%) of 3 as amorphous hydrochloride.

Example 2

Synthesis of N-(5-chloro-2-methoxyphenyl)-2-{10-[4-(2-hydroxyethyl)-piperazin-1-yl]-3,4-dihydro-1H-benzo[b]-1,6-naphthyridin-2-yl}acetamide (7)

ture, which is extracted by shaking, and the phases are separated. The aqueous phase is extracted again by shaking with ethyl acetate, the combined organic phases are then washed with saturated sodium chloride solution, dried over MgSO4, filtered off and evaporated to dryness in vacuo. The crude product is purified by chromatography on silicagel 60 with cyclohexane and ethyl acetate as eluents. The corresponding fractions are evaporated to dryness in vacuo, giving 3.1 g (73.8%) of 4 as yellowish crystals.

b. 0.3 g (0.94 mmol) of 4, 0.16 ml (1.3 mmol) of 2-piperazin-1-yl-ethanol and 0.25 g (2.6 mmol) of phenol are heated at 120° C. in the microwave apparatus for 30 min. 50 ml of ethyl acetate are added to the reaction mixture, which is extracted 2× with 10 ml of 1N NaOH each time. The organic phase is then washed 3× with saturated sodium chloride solution, dried over Na2SO4, filtered off and evaporated to dryness in vacuo, giving a yellow oil, which crystallises out: 0.3 g (77.4%) of 5.

c. 10 ml of 6N HCl in methanol are added to 90 mg (0.22 mmol) of 5, and the mixture is stirred at room temperature for 1 hour. The mixture is then evaporated to dryness in vacuo, giving 20 mg (29%) of 6 as yellow amorphous substance.

d. 20 mg (0.064 mmol) of 6, 18 mg (0.064 mmol) of 2-bromo-N-(5-chloro-2-methoxyphenyl)acetamide and 62.6

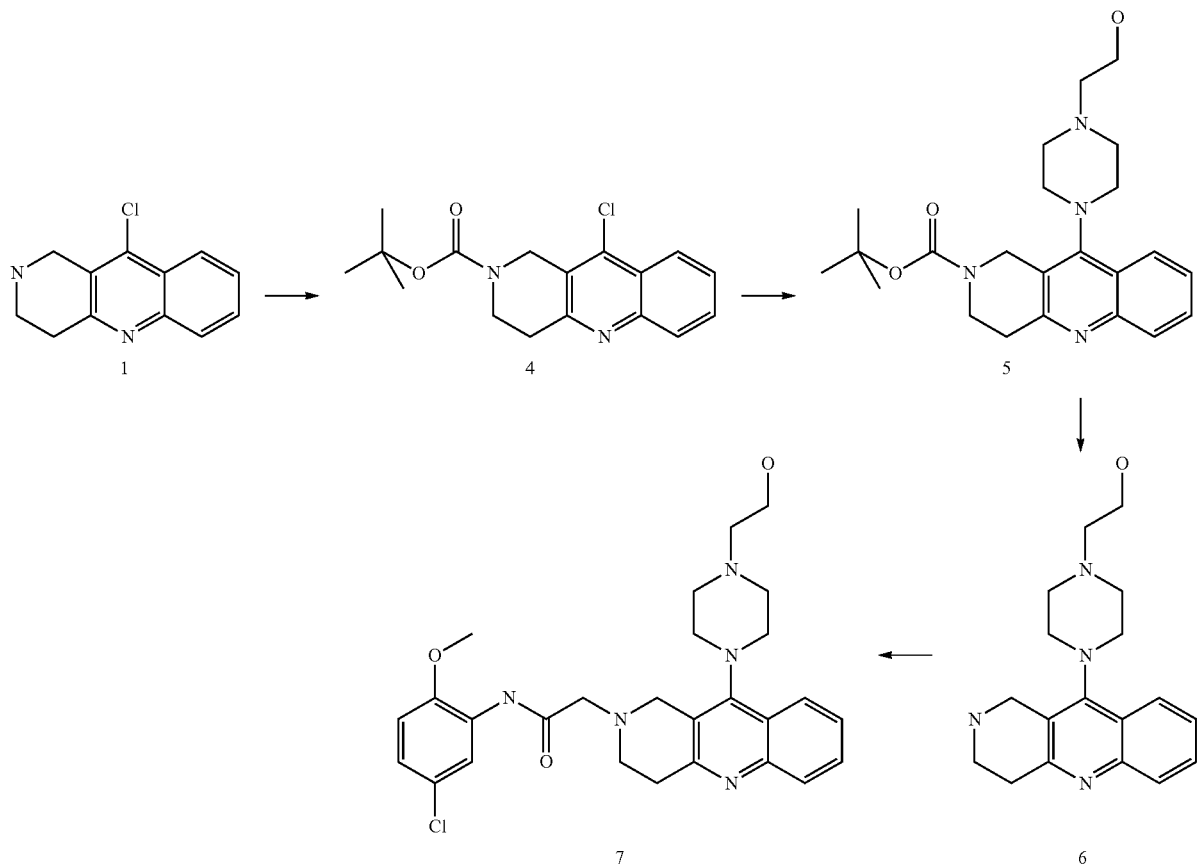

a. 2.90 g (13.3 mmol) of 1 (synthesis is described in Example 1) are dissolved in 130 ml of dioxane. 50 ml of 1N sodium hydrogencarbonate solution and 3.4 ml (15.9 mmol) of di-tert-butyl dicarbonate, mixed with 30 ml of dioxane, are added Ethyl acetate and water are added to the reaction mixmg (0.192 mmol) of caesium carbonate are stirred in 8 ml of DMF for 18 hours. Ethyl acetate is then added to the batch. The mixture is washed once with water and 3× with saturated sodium chloride solution, the organic phase is subsequently dried using Na2SO4, filtered off and evaporated to dryness in vacuo. The residue is purified by means of preparative HPLC. Subsequent lyophilisation gives 17.7 mg (52%) of 7 as brown crystals.

Example 3

Synthesis of 10-(2-dimethylaminoethylamino)-3,4-dihydro-1H-benzo[b]-1,6-naphthyridine-2-carboxylic acid (5-chloro-2-methoxyphenylcarbamoyl)-methyl ester

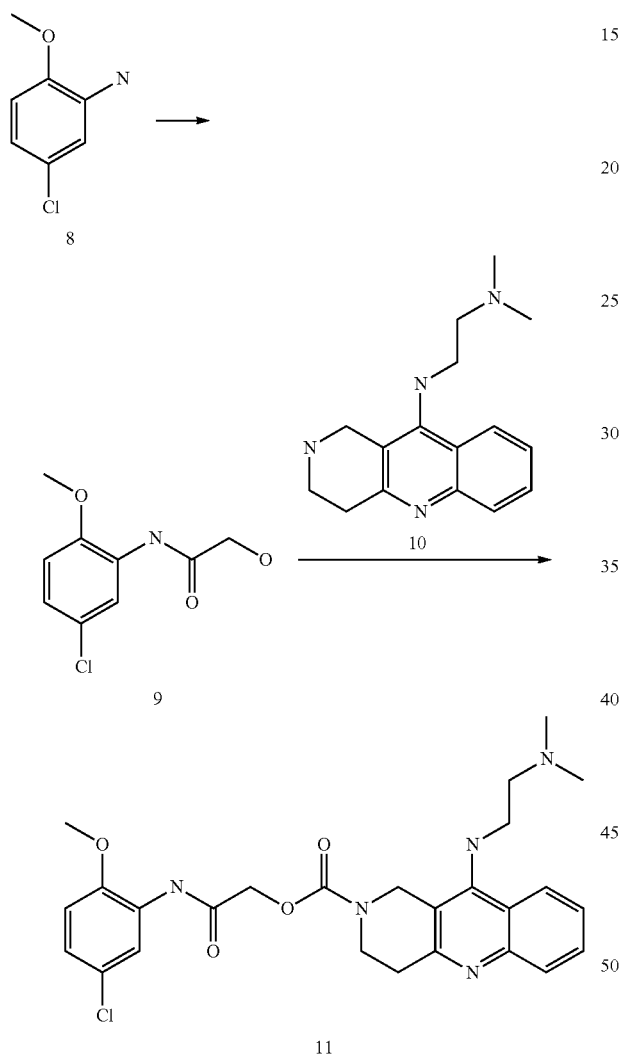

Firstly, the amide 9 is formed from glycolic acid and 5-chloro-2-methoxyphenylamine 8 using a suitable amide-coupling process, for example TBTU, HOBt (1-hydroxybenzotriazole hydrate), NMM (4-methylmorpholine) in DMF. This amide 9 is stirred in a suitable solvent (for example DMF) with 1,1'-carbonyldiimidazole at RT for several hours. Subsequent addition of 10 to the reaction mixture and stirring again at RT for several hours gives 11.

An overview of further compounds of the invention synthesised analogously, including the physical-chemical parameters of all compounds of the invention, is given in Table 2.

TABLE 2

| Compound No. | Chemical Name | Rt [min] (HPLC method)* | ESI [M + 1]+ |
|---|---|---|---|
| 1 | N-(5-Chloro-2-methoxyphenyl)-2-[10-(1-methylpiperidin-4-ylamino)-3,4-dihydro-1H-benzo[b]-1,6-naphthyridin-2-yl]acetamide | 2.16 (C) | 495 |
| 2 | 2-(10-Amino-3,4-dihydro-1H-benzo[b]-1,6-naphthyridin-2-yl)-N-(5-chloro-2-methoxyphenyl)-acetamide | 2.43 (A) | 398 |
| 3 | 2-(10-Amino-3,4-dihydro-1H-benzo[b]-1,6-naphthyridin-2-yl)-N-(2,5-dichlorophenyl)-acetamide | 2.46 (A) | 402 |
| 4 | N-(5-Chloro-2-methoxy-phenyl)-2-[10-(2-hydroxyethylamino)-3,4-dihydro-1H-benzo[b]-1,6-naphthyridin-2-yl]-acetamide | 2.43 (A) | 442 |
| 5 | N-(5-Chloro-2-methoxyphenyl)-2-[10-(2-dimethylamino-ethylamino)-3,4-dihydro-1H-benzo[b]-1,6-naphthyridin-2-yl]acetamide | 2.15 (B) | 469 |
| 6 | 10-(2-Dimethylamino-ethylamino)-3,4-dihydro-1H-benzo[b]-1,6-naphthyridine-2-carboxylic acid (5-chloro-2-methoxyphenyl-carbamoyl)methyl ester | 2.11 (B) | 513 |
| 7 | 10-(2-Hydroxy-ethylamino)-3,4-dihydro-1H-benzo[b]-1,6-naphthyridine-2-carboxylic acid (5-chloro-2-methoxyphenyl-carbamoyl)methyl ester | 2.43 (A) | 486 |
| 8 | N-(5-Chloro-2-methoxyphenyl)-2-[10-(methylcarbamoylmethyl-amino)-3,4-dihydro-1H-benzo[b]-1,6-naphthyridin-2-yl]acetamide | 2.67 (C) | 469 |
| 9 | N-(5-Chloro-2-methoxyphenyl)-2-[10-(dimethylcarbamoyl-methylamino)-3,4-dihydro-1H-benzo[b]-1,6-naphthyridin-2-yl]-acetamide | 2.83 (C) | 483 |
| 10 | N-(5-Chloro-2-methoxyphenyl)-2-{10-[4-(2-hydroxyethyl)piperazin-1-yl]-3,4-dihydro-1H-benzo[b]-1,6-naphthyridin-2-yl}acetamide | 2.27 (A) | 511 |
| 11 | 2-{10-[(1H-Benzimidazol-2-ylmethyl)amino]-3,4-dihydro-1H-benzo[b]-1,6-naphthyridin-2-yl}-N-(5-chloro-2-methoxy-phenyl)acetamide | 2.80 (C) | 527 |
| 12 | N-(5-Chloro-2-methoxyphenyl)-2-[10-(2-oxo-2-pyrrolidin-1-yl-ethylamino)-3,4-dihydro-1H-benzo[b]-1,6-naphthyridin-2-yl]acetamide | 2.91 (C) | 509 |
| 13 | N-(5-Chloro-2-methoxyphenyl)-2-[10-(2-oxo-2-piperidin-1-yl- | 3.15 (C) | 523 |

TABLE 2-continued

| Compound No. | Chemical Name | Rt [min] (HPLC method)* | ESI [M + 1]+ |
|---|---|---|---|
| | ethylamino)-3,4-dihydro-1H-benzo[b]-1,6-naphthyridin-2-yl]acetamide | | |
| 14 | N-(5-Chloro-2-methoxyphenyl)-2-[10-(2-morpholin-4-yl-2-oxo-ethylamino)-3,4-dihydro-1H-benzo[b]-1,6-naphthyridin-2-yl]acetamide | 2.80 (C) | 525 |
| 15 | N-(5-Chloro-2-methoxyphenyl)-2-[10-(cyclohexylcarbamoyl-methylamino)-3,4-dihydro-1H-benzo[b]-1,6-naphthyridin-2-yl]-acetamide | 3.20 (C) | 537 |
| 16 | N-(5-Chloro-2-methoxyphenyl)-2-{10-[2-(4-methylpiperazin-1-yl)-2-oxoethylamino]-3,4-dihydro-1H-benzo[b]-1,6-naphthyridin-2-yl}-acetamide | 2.29 (C) | 538 |
| 17 | N-(5-Chloro-2-methoxyphenyl)-2-{10-[2-(4-isopropylpiperazin-1-yl)-2-oxoethylamino]-3,4-dihydro-1H-benzo[b]-1,6-naphthyridin-2-yl}-acetamide | 2.32 (C) | 566 |
| 18 | N-(5-Chloro-2-methoxyphenyl)-2-[10-(diethylcarbamoylmethyl-amino)-3,4-dihydro-1H-benzo[b]-1,6-naphthyridin-2-yl]acetamide | 3.15 (C) | 511 |
| 19 | 2-{10-[2-(4-Benzyl-piperazin-1-yl)-2-oxo-ethylamino]-3,4-dihydro-1H-benzo[b]-1,6-naphthyridin-2-yl}-N-(5-chloro-2-methoxyphenyl)-acetamide | 2.59 (C) | 614 |
| 20 | N-(5-Chloro-2-methoxy-phenyl)-2-[10-(pyridin-4-ylamino)-3,4-dihydro-1H-benzo[b]-1,6-naphthyridin-2-yl]acetamide | 2.53 (C) | 475 |
| 21 | N-(5-Chloro-2-methoxy-phenyl)-2-[10-(pyridin-3-ylamino)-3,4-dihydro-1H-benzo[b]-1,6-naphthyridin-2-yl]acetamide | 2.72 (C) | 475 |
| 22 | N-(5-Chloro-2-methoxy-phenyl)-2-(10-phenyl-amino-3,4-dihydro-1H-benzo[b]-1,6-naphthyridin-2-yl)acetamide | 3.25 (C) | 474 |
| 23 | N-(5-Chloro-2-methoxy-phenyl)-2-[10-(pyridin-2-ylamino)-3,4-dihydro-1H-benzo[b]-1,6-naphthyridin-2-yl]acetamide | 2.96 (C) | 475 |
| 24 | N-(5-Chloro-2-methoxy-phenyl)-2-[10-(4-methoxyphenylamino)-3,4-dihydro-1H-benzo[b]-1,6-naphthyridin-2-yl]-acetamide | 3.25 (C) | 504 |

The $^1$H-NMR data for selected compounds of the invention are shown below:

Compound 2
$^1$H NMR (500 MHz, DMSO) δ=8.56 (d, J=8.5, 1H), 8.20 (t, J=3.8, 1H), 7.99 (t, J=7.7, 1H), 7.92 (d, J=8.4, 1H), 7.72 (t, J=7.8, 1H), 7.22 (dd, J=8.8, 2.5, 1H), 7.14 (d, J=8.9, 1H), 4.54 (m, 4H), 3.90 (s, 3H), 3.84 (t, J=5.9, 2H), 3.46 (t, J=6.0, 2H)

Compound 4
$^1$H NMR (400 MHz, DMSO) δ=8.50 (t, J=13.4, 1H), 8.10 (d, J=2.2, 1H), 7.94-7.77 (m, 2H), 7.71-7.52 (m, 1H), 7.20-6.93 (m, 2H), 4.91-4.49 (m, 4H), 4.04-3.62 (m, 9H), 3.17 (m, 2H).

Compound 7
$^1$H NMR (400 MHz, DMSO) δ=8.50 (t, J=13.4, 1H), 8.10 (d, J=2.2, 1H), 7.94-7.77 (m, 2H), 7.71-7.52 (m, 1H), 7.20-6.93 (m, 2H), 4.91-4.49 (m, 4H), 4.04-3.62 (m, 9H), 3.17 (m, 2H).

Compound 8
$^1$H NMR (500 MHz, DMSO) δ=8.40 (d, J=8.6, 1H), 8.20 (d, J=2.5, 1H), 7.96 (m, 2H), 7.75-7.66 (m, 1H), 7.21 (dd, J=8.8, 2.6, 1H), 7.17-7.10 (m, 1H), 4.72 (s, 2H), 4.52 (t, J=16.1, 4H), 3.97-3.85 (2, 3H), 3.81 (t, J=6.2, 2H), 3.47 (m, 2H), 2.71 (s, 3H).

Compound 9
$^1$H NMR (500 MHz, DMSO) δ=8.45 (d, J=8.6, 1H), 8.18 (d, J=2.5, 1H), 8.01 (t, J=7.4, 1H), 7.94 (d, J=7.8, 1H), 7.73 (t, J=7.8, 1H), 7.22 (dd, J=8.8, 2.5, 1H), 7.14 (d, J=8.9, 1H), 4.82 (s, 2H), 4.73 (s, 2H), 4.55 (s, 2H), 3.95-3.86 (m, 3H), 3.86 (s, 2H), 3.47 (dd, J=14.0, 7.6, 2H), 3.08 (d, J=11.5, 3H), 2.95 (d, J=11.5, 3H).

Compound 11
$^1$H NMR (500 MHz, DMSO) δ=8.44 (d, J=8.7, 1H), 8.10-7.93 (m, 3H), 7.76 (m, 2H), 7.69 (dd, J=11.0, 4.2, 1H), 7.54-7.48 (m, 2H), 7.14 (dd, J=8.8, 2.6, 1H), 7.05 (d, J=8.9, 1H), 5.63 (s, 2H), 4.76 (s, 2H), 4.51 (d, J=19.6, 2H), 3.88-3.75 (m, 5H), 3.67-3.45 (m, 2H).

Compound 12
$^1$H NMR (400 MHz, DMSO) δ=8.47 (d, J=8.6, 1H), 8.21 (d, J=2.6, 1H), 8.03-7.93 (m, 2H), 7.73 (ddd, J=8.4, 6.4, 1.8, 1H), 7.21 (dd, J=8.8, 2.5, 1H), 7.12 (d, J=8.9, 1H), 4.80 (s, 2H), 4.75 (s, 2H), 4.59 (s, 2H), 3.90 (s, 3H), 3.86 (m, 2H), 3.52 (m, 4H), 3.41 (t, J=6.9, 2H), 2.01-1.89 (m, 2H), 1.89-1.76 (m, 2H).

Compound 13
$^1$H NMR (400 MHz, DMSO) δ=8.48 (d, J=8.7, 1H), 8.22 (m, 1H), 8.04-7.92 (m, 2H), 7.72 (ddd, J=8.4, 6.3, 1.9, 1H), 7.21 (dd, J=8.8, 2.5, 1H), 7.12 (d, J=8.9, 1H), 4.83 (2 s, 4H), 4.61 (s, 2H), 3.93 (s, 3H), 3.85 (m, 2H), 3.64-3.36 (m, 6H), 1.57 (m, 6H).

Compound 14
$^1$H NMR (400 MHz, DMSO) δ=8.41 (d, J=8.7, 1H), 8.12 (dd, J=11.0, 7.0, 1H), 7.97-7.86 (m, 2H), 7.71-7.61 (m, 1H), 7.13 (m, 1H), 7.04 (d, J=8.9, 1H), 4.82 (s, 2H), 4.72 (s, 2H), 4.53 (s, 2H), 3.83 (s, 3H), 3.81 (s, 2H), 3.67-3.40 (m, 10H).

Compound 16
$^1$H NMR (500 MHz, DMSO) δ=8.51 (d, J=8.7, 1H), 8.19 (d, J=3.8, 1H), 8.06-7.94 (m, 2H), 7.75 (ddd, J=8.4, 5.8, 2.4, 1H), 7.21 (dd, J=8.8, 2.5, 1H), 7.12 (d, J=8.9, 1H), 5.17-5.04 (m, 1H), 4.97-4.81 (m, 3H), 4.65 (s, 2H), 4.49 (d, J=14.1, 1H), 4.27 (d, J=13.4, 1H), 3.97-3.78 (m, 5H), 3.69-3.48 (m, 5H), 3.31-3.00 (m, 3H), 2.92 (d, J=5.1, 3H).

Compound 17
$^1$H NMR (500 MHz, DMSO) δ=8.49 (d, J=8.7, 1H), 8.20 (m, 1H), 7.99 (m, 2H), 7.73 (t, J=7.1, 1H), 7.21 (dd, J=8.8, 2.5, 1H), 7.11 (d, J=8.9, 1H), 5.04 (d, J=17.8, 1H), 4.90 (d, J=16.6, 1H), 4.77 (s, 2H), 4.59 (s, 3H), 4.25 (d, J=13.0, 1H), 3.90 (s, 3H), 3.87 (m, 2H), 3.67-3.39 (m, 6H), 3.18 (d, J=17.1, 2H), 3.00 (s, 1H), 1.42-1.22 (m, 6H).

Compound 18
$^1$H NMR (400 MHz, DMSO) δ=8.44-8.33 (m, 1H), 8.16 (d, J=2.5, 1H), 7.89 (m, 2H), 7.63 (m, 1H), 7.13 (dd, J=8.7, 2.3, 1H), 7.09-7.00 (m, 1H), 4.86-4.66 (m, 4H), 4.61-4.47 (m, 2H), 3.91-3.71 (m, 5H), 3.37 (m, 6H), 1.24-1.10 (m, 3H), 1.02 (t, J=7.1, 3H).

Compound 22

$^1$H NMR (500 MHz, DMSO) δ=8.28 (d, J=8.6, 1H), 8.05 (d, J=3.8, 1H), 8.02-7.93 (m, 2H), 7.63 (ddd, J=8.4, 6.3, 1.8, 1H), 7.46-7.38 (m, 2H), 7.28 (dd, J=13.9, 6.5, 1H), 7.21 (dd, J=13.3, 6.6, 2H), 7.18-7.11 (m, 1H), 7.04 (d, J=8.9, 1H), 4.31 (s, 2H), 4.11 (s, 2H), 3.88-3.72 (m, 4H), 3.58-3.46 (m, 3H).

Compound 23

$^1$H NMR (500 MHz, DMSO) δ=8.24 (d, J=8.5, 1H), 8.16 (d, J=4.2, 1H), 8.08 (d, J=8.4, 1H), 8.05-7.98 (m, 2H), 7.91-7.82 (m, 1H), 7.71 (t, J=7.6, 1H), 7.20-7.11 (m, 2H), 7.06 (m, 2H), 4.39 (d, J=13.5, 4H), 3.85 (t, J=8.3, 2H), 3.81 (s, 3H), 3.67-3.55 (m, 2H).

Compound 24

$^1$H NMR (500 MHz, DMSO) δ=8.26 (d, J=8.7, 1H), 8.08 (m, 1H), 7.95-7.84 (m, 2H), 7.55 (t, J=7.4, 1H), 7.17 (d, J=8.7, 2H), 7.12-7.06 (m, 1H), 6.99 (d, J=8.9, 1H), 6.94 (d, J=8.7, 2H), 4.31 (s, 2H), 4.06 (s, 2H), 3.79 (s, 3H), 3.75 (t, J=6.3, 2H), 3.70 (s, 3H), 3.47 (t, J=6.5, 2H).

The following analytical methods were used for the determination of the physical-chemical parameters shown above:

ESI: Electrospray ionisation mass spectrometry (M+H)$^+$

*(A): HPLC method: 1__100__2 Speed (instrument: LaChrom)
Column: Chromolith Performance RP18e 100-3 mm
Flow rate: 2 ml/min (pump: L-7100)
Solvent A: water+0.01% of TFA
Solvent B: acetonitrile+0.01% of TFA
Wavelength: 220 nm (detector: L-7455)
0-0.2 100% of A, 0.2-3.7 to 100% of B, 3.7-4.4 100% of B, 4.5-5.0 100% of A (B): HPLC method: polar.M (instrument: Agilent 1100 series)
Column: Chromolith Speed Rod RP18e-50-4.6
Flow rate: 2.4 ml/min
Solvent A: water+0.05% of HCOOH
Solvent B: acetonitrile+0.04% of HCOOH
WL: 220 nm
Gradient: 0-2.8 min: 4% of B to 100% of B, 2.6-3.3 min: 100% of B (C): HPLC method: column: Chromolith SpeedROD, 50×4.6 mm2
(Order No. ^1.51450.0001) from Merck
Gradient: 5.0 min, t=0 min, A:B=95:5, t=4.4 min: A:B=25:75, t=4.5 min tot=5.0 min: A:B=0:100
Flow rate:3.00 ml/min, eluent A: water+0.01% of HCOOH (formic acid)
Eluent B: acetonitrile+0.01% of HCOOH, wavelength: 220 nm II. Autotaxin Test (Enzyme Test)

Test Description

The autotaxin activity is measured indirectly using Amplex Red reagent. Amplex Red is measured here as fluorogenic indicator for the $H_2O_2$ formed. In detail, autotaxin converts the substrate lysophosphatidylcholine (LPC) into phosphocholine and lysophosphatidic acid (LPA). After this reaction, the phosphocholine is reacted with alkaline phosphatase to give inorganic phosphate and choline. In the next step, choline is oxidised by choline oxidase to give betaine, with formation of $H_2O_2$. $H_2O_2$ reacts with Amplex Red reagent in the presence of peroxidase (horseradish peroxidase) in a 1:1 stoichiometry and forms the highly fluorescent resorufin. The fluorescence is measured in a reaction-dependent kinetic mode in order that fluorescent signals from possible other fluorescent substances which are not involved in the reaction can be corrected out.

Test Procedure 1.5 μl of a standard solution or of the test substances (compounds of the invention) in individual concentrations dissolved in 20 mM Hepes pH 7.2 with a maximum of 7.7% of DMSO are pre-incubated together with 10 μl (16 ng) of highly purified recombinant autotaxin in a black microtitre plate provided with 384 wells at 22° C. for 30 min. The reaction is then initiated by addition of 5 μl of L-α-lysophosphatidylcholine (LPC), where the final concentration of LPC is 75 μM. The mixture is incubated at 37° C. for 90 min. After the incubation, Amplex Red reagent, peroxidase (horseradish peroxidase) and choline oxidase is added, and the fluorescence is immediately measured at 612 nm with excitation of 485 nm in a "Tecan Ultra multimode" reader. The activity of autotaxin is calculated indirectly via detection of the $H_2O_2$ formed.

Material:

Microtitre plate: PS microplate, 384 wells, small volume, black Corning, Cat#3677
Protein: recombinant autotaxin (Baculovirale Hi5 Expression)
Substrate: L-a-lysophosphatidylcholine (chicken egg)); Avanti Polar Lipids #830071 P
Standard: C14 LPA, Avanti Polar Lipids, Cat#857120P
Detection reagent: Amplex Red reagent; Invitrogen #A12222; dissolved in 1.923 ml of DMSO peroxidase type VI-A (horseradish) from Sigma #P6782; dissolved in 7.45 ml of test buffer, choline oxidase; Sigma #C5896; dissolved in 2.47 ml of test buffer
Detection reagent mix: 1:100 dilution of Amplex Red Reagenzt in test buffer
Test buffer: 200 mM Tris HCl, Merck, Cat #1.08219, pH 7.9, 0.1% BSA, lipid-free, Roche Cat#775835

Pharmacological Data

Autotaxin Inhibition ($IC_{50}$ ranges: A: <100 nM, B: 100 nM-1000 nM, C: >1000 nM)

TABLE 3

| Compound according to the invention | $IC_{50}$; % (ctrl 3E-5M) |
|---|---|
| N-(5-Chloro-2-methoxyphenyl)-2-[10-(1-methylpiperidin-4-ylamino)-3,4-dihydro-1H-benzo[b]-1,6-naphthyridin-2-yl]acetamide | B |
| 2-(10-Amino-3,4-dihydro-1H-benzo[b]-1,6-naphthyridin-2-yl)-N-(5-chloro-2-methoxyphenyl)acetamide | C |
| 2-(10-Amino-3,4-dihydro-1H-benzo[b]-1,6-naphthyridin-2-yl)-N-(2,5-dichlorophenyl)acetamide | 79% |
| N-(5-Chloro-2-methoxyphenyl)-2-[10-(2-hydroxyethylamino)-3,4-dihydro-1H-benzo[b]-1,6-naphthyridin-2-yl]acetamide | B |
| N-(5-Chloro-2-methoxyphenyl)-2-[10-(2-dimethylaminoethylamino)-3,4-dihydro-1H-benzo[b]-1,6-naphthyridin-2-yl]acetamide | B |
| 10-(2-Dimethylaminoethylamino)-3,4-dihydro-1H-benzo[b]-1,6-naphthyridine-2-carboxylic acid (5-chloro-2-methoxyphenylcarbamoyl)methyl ester | -9% |
| 10-(2-Hydroxyethylamino)-3,4-dihydro-1H-benzo[b]-1,6-naphthyridine-2-carboxylic acid (5-chloro-2-methoxyphenylcarbamoyl)methyl ester | C |
| N-(5-Chloro-2-methoxyphenyl)-2-[10-(methylcarbamoylmethylamino)-3,4-dihydro-1H-benzo[b]-1,6-naphthyridin-2-yl]acetamide | B |
| N-(5-Chloro-2-methoxyphenyl)-2-[10-(dimethylcarbamoylmethylamino)-3,4-dihydro-1H-benzo[b]-1,6-naphthyridin-2-yl]acetamide | B |

TABLE 3-continued

| Compound according to the invention | IC$_{50}$; % (ctrl 3E−5M) |
|---|---|
| N-(5-Chloro-2-methoxyphenyl)-2-{10-[4-(2-hydroxyethyl)-piperazin-1-yl]-3,4-dihydro-1H-benzo[b]-1,6-naphthyridin-2-yl}acetamide | B |
| 2-{10-[(1H-Benzimidazol-2-ylmethyl)amino]-3,4-dihydro-1H-benzo[b]-1,6-naphthyridin-2-yl}-N-(5-chloro-2-methoxyphenyl)acetamide | C |
| N-(5-Chloro-2-methoxyphenyl)-2-[10-(2-oxo-2-pyrrolidin-1-ylethylamino)-3,4-dihydro-1H-benzo[b]-1,6-naphthyridin-2-yl]acetamide | B |
| N-(5-Chloro-2-methoxyphenyl)-2-[10-(2-oxo-2-piperidin-1-ylethylamino)-3,4-dihydro-1H-benzo[b]-1,6-naphthyridin-2-yl]acetamide | B |
| N-(5-Chloro-2-methoxyphenyl)-2-[10-(2-morpholin-4-yl-2-oxoethylamino)-3,4-dihydro-1H-benzo[b]-1,6-naphthyridin-2-yl]acetamide | B |
| N-(5-Chloro-2-methoxyphenyl)-2-[10-(cyclohexyl-carbamoylmethylamino)-3,4-dihydro-1H-benzo[b]-1,6-naphthyridin-2-yl]acetamide | C |
| N-(5-Chloro-2-methoxyphenyl)-2-{10-[2-(4-methyl-piperazin-1-yl)-2-oxoethylamino]-3,4-dihydro-1H-benzo-[b]-1,6-naphthyridin-2-yl}acetamide | B |
| N-(5-Chloro-2-methoxyphenyl)-2-{10-[2-(4-isopropyl-piperazin-1-yl)-2-oxoethylamino]-3,4-dihydro-1H-benzo-[b]-1,6-naphthyridin-2-yl}acetamide | B |
| N-(5-Chloro-2-methoxyphenyl)-2-[10-(diethyl-carbamoylmethylamino)-3,4-dihydro-1H-benzo[b]-1,6-naphthyridin-2-yl]acetamide | B |
| 2-{10-[2-(4-Benzylpiperazin-1-yl)-2-oxoethylamino]-3,4-dihydro-1H-benzo[b]-1,6-naphthyridin-2-yl}-N-(5-chloro-2-methoxyphenyl)acetamide | B |
| N-(5-Chloro-2-methoxyphenyl)-2-[10-(pyridin-4-ylamino)-3,4-dihydro-1H-benzo[b]-1,6-naphthyridin-2-yl]acetamide | C |
| N-(5-Chloro-2-methoxyphenyl)-2-[10-(pyridin-3-ylamino)-3,4-dihydro-1H-benzo[b]-1,6-naphthyridin-2-yl]acetamide | C |
| N-(5-Chloro-2-methoxyphenyl)-2-(10-phenylamino-3,4-dihydro-1H-benzo[b]-1,6-naphthyridin-2-yl)acetamide | C |
| N-(5-Chloro-2-methoxyphenyl)-2-[10-(pyridin-2-ylamino)-3,4-dihydro-1H-benzo[b]-1,6-naphthyridin-2-yl]acetamide | C |
| N-(5-Chloro-2-methoxyphenyl)-2-[10-(4-methoxy-phenylamino)-3,4-dihydro-1H-benzo[b]-1,6-naphthyridin-2-yl]acetamide | C |

The invention claimed is:

1. A compound of formula (I)

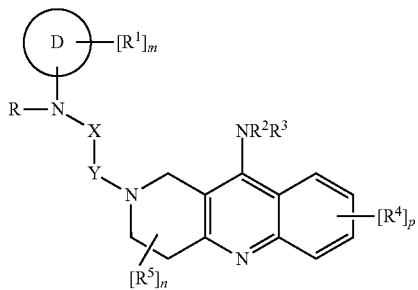

(I)

in which:

D denotes Ar or Het,

Ar denotes unsubstituted or mono- or polysubstituted phenyl, indanyl, naphthyl or biphenyl, Het denotes a mono- or bicyclic saturated, partially unsaturated or aromatic heterocycle having 1, 2, 3 or 4 N, O and/or S atoms, which may be unsubstituted or mono- or polysubstituted, X, Y each, independently of one another, is absent, denotes —CH$_2$—, —(CH$_2$)$_2$—, —C(O)—, —CHOH— or —CH$_2$OC(O)—, where only one of the radicals X or Y may be absent, R in each case, independently of one another, denote H, A, Cyc, (CH$_2$)$_g$Ar or (CH$_2$)$_q$Het and may be mono- or polysubstituted by R$^6$, where in A and Cyc, the C chain and C ring respectively may also be interrupted by O, R$^1$ in each case, independently of one another, denote R, F, Cl, Br, I, OH, =O, CN, NO$_2$, NRR, NHC(O)R, NHSO$_2$R, OR, C(O)R, C(O)NRR, CF$_3$, OCF$_3$, SCF$_3$, SO$_2$CH$_3$, SO$_3$R, SO$_2$R, SO$_2$NR, SR, OA, A, phenyl and may be mono- or polysubstituted by R$^6$, R$^2$, R$^3$ each, independently of one another, denote R, where R$^2$ and R$^3$ may alternatively together also form Cyc or Het, each of which may in turn be mono- or polysubstituted by R$^6$, R$^4$ in each case, independently of one another, denote R, F, Cl, Br, I, OH, =O, CN, NO$_2$, NRR, NHC(O)R, NHSO$_2$R, OR, C(O)R, C(O)NRR, CF$_3$, OCF$_3$, SCF$_3$, SO$_2$CH$_3$, SO$_3$R, SO$_2$R, SO$_2$NR, SR, OA, A, phenyl and may be mono- or polysubstituted by R$^6$, R$^5$ in each case, independently of one another, denote R, F, Cl, Br, I, OH, =O, CN, NO$_2$, NRR, NHC(O)R, NHSO$_2$R, OR, C(O)R, C(O)NRR, CF$_3$, OCF$_3$, SCF$_3$, SO$_2$CH$_3$, SO$_3$R, SO$_2$R, SO$_2$NR, SR, OA, A, phenyl and may be mono- or polysubstituted by R$^6$, R$^6$ in each case, independently of one another, denote R, F, Cl, Br, I, OH, =O, CN, NO$_2$, NRR, NHC(O)R, NHSO$_2$R, OR, C(O)R, C(O)NRR, CF$_3$, OCF$_3$, SCF$_3$, SO$_2$CH$_3$, SO$_3$R, SO$_2$R, SO$_2$NR, SR, OA, A, phenyl and, so long as a substitution is chemically possible, may be mono- or polysubstituted by R, F, Cl, Br, I, OH, =O, CN, NO$_2$, NRR, NHC(O)R, NHSO$_2$R, OR, C(O)R, C(O)NRR, CF$_3$, OCF$_3$, SCF$_3$, SO$_2$CH$_3$, SO$_3$R, SO$_2$R, SO$_2$NR, SR, OA, A, phenyl, A denotes linear or branched alkyl having 1, 2, 3, 4, 5, 6, 7 or 8 C atoms, in which 1, 2, 3, 4, 5, 6 or 7 H atoms may be replaced by OR, CN, NRR, F and/or Cl and/or in which one or two non-adjacent CH$_2$ groups may be replaced by O, NH, S, SO, SO$_2$ and/or by CH=CH groups, Cyc denotes cyclic alkyl having 3, 4, 5, 6, 7, 8, 9, 10, 11, 12, 13 or 14 C atoms, m denotes 0, 1, 2, 3, 4, or 5, n denotes 0, 1, 2, or 3, p denotes 0, 1, 2, 3, or 4, q denotes 0, 1, or 2, or pharmaceutically usable salts, solvates or stereoisomers thereof, including mixtures thereof in all ratios.

2. A compound according to claim 1 in which

D denotes Ar,

Ar denotes unsubstituted or mono- or polysubstituted phenyl,

X, Y each, independently of one another, denote —CH$_2$—, —C(O)— or —CH$_2$OC(O)—, R$^1$ in each case, independently of one another, denote F, Cl, OA or OCH$_3$, R$^2$, R$^3$ each, independently of one another, denote H, Ar, Ar monosubstituted by OA, Het, Het monosubstituted by A, CH$_2$-Het, A, A monosubstituted by OH or by NRR or by CO—NRR or by Het or by CO—R, or each, independently of one another, denote 1-methylpiperidin-4-yl, 2-hydroxyethyl, 2-dimethylaminoethyl, methylcarbamoylmethyl, dimethylcarbamoylmethyl, 1H-benzimidazol-2-ylmethyl, 2-oxo-2-pyrrolidin-1-yl-ethyl, 2-oxo-2-piperidin-1-ylethyl, 2-morpholin-4-yl-2-oxoethyl, cyclohexylcarbamoylmethyl, 2-(4-methylpiperazin-1-yl)-2-oxo-ethyl, 2-(4-isopropylpiperazin-1-yl)-2-oxoethyl, diethylcarbamoylmethyl, 2-(4-benzylpiperazin-1-yl)-2-oxoethyl, 3-oxo-3-piperidin-1-ylpropyl, pyridin-4-yl, pyridin-3-yl, phenyl, pyridin-2-yl or 4-methoxyphenyl, where $R^2$ and $R^3$ may alternatively together also form 4-(2-hydroxyethyl)-piperazin-1-yl, m denotes 2, n denotes 0, p denotes 0, q denotes 0 or 1, Het, R, $R^6$, A and Cyc have the meanings indicated in claim 1, or pharmaceutically usable salts, solvates and or stereoisomers thereof, including mixtures thereof in all ratios.

3. A compound according claim 1,

| Compound No. | Chemical Structure | Chemical Name |
|---|---|---|
| 1 | 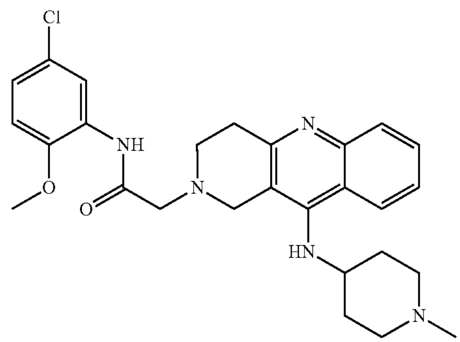 [SMILES: COc1ccc(Cl)cc1NC(=O)CN1CCc2nc3ccccc3c(NC3CCN(C)CC3)c2C1] | N-(5-Chloro-2-methoxyphenyl)-2-[10-(1-methylpiperidin-4-ylamino)-3,4-dihydro-1H-benzo[b]-1,6-naphthyridin-2-yl]acetamide |
| 2 | 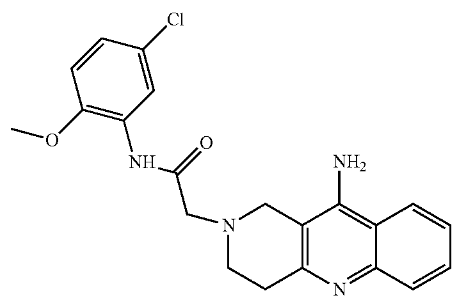 [SMILES: COc1ccc(Cl)cc1NC(=O)CN1CCc2nc3ccccc3c(N)c2C1] | 2-(10-Amino-3,4-dihydro-1H-benzo[b]-1,6-naphthyridin-2-yl)-N-(5-chloro-2-methoxyphenyl)acetamide |
| 3 | 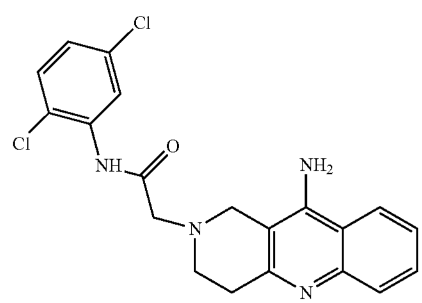 [SMILES: Nc1c2c(nc3ccccc13)CCN(CC(=O)Nc1cc(Cl)ccc1Cl)C2] | 2-(10-Amino-3,4-dihydro-1H-benzo[b]-1,6-naphthyridin-2-yl)-N-(2,5-dichlorophenyl)-acetamide |
| 4 | 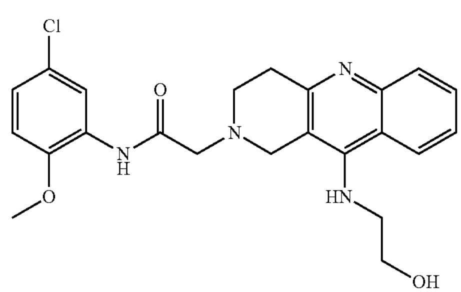 [SMILES: COc1ccc(Cl)cc1NC(=O)CN1CCc2nc3ccccc3c(NCCO)c2C1] | N-(5-Chloro-2-methoxyphenyl)-2-[10-(2-hydroxyethylamino)-3,4-dihydro-1H-benzo[b]-1,6-naphthyridin-2-yl]acetamide |

| Compound No. | Chemical Structure | Chemical Name |
|---|---|---|
| 5 | 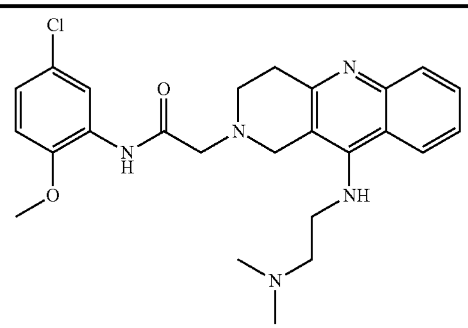 | N-(5-Chloro-2-methoxyphenyl)-2-[10-(2-dimethylaminoethyl-amino)-3,4-dihydro-1H-benzo[b]-1,6-naphthyridin-2-yl]acetamide |
| 6 | 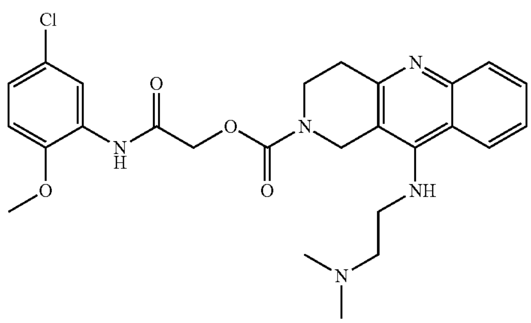 [SMILES: COc1ccc(Cl)cc1NC(=O)COC(=O)N1CCc2nc3ccccc3c(NCCN(C)C)c2C1] | 10-(2-Dimethylamino-ethylamino)-3,4-dihydro-1H-benzo[b]-1,6-naphthyridine-2-carboxylic acid (5-chloro-2-methoxy-phenylcarbamoyl)methyl ester |
| 7 | 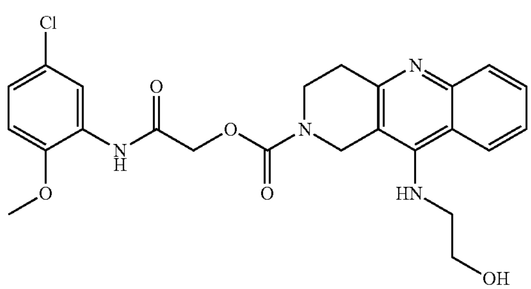 [SMILES: COc1ccc(Cl)cc1NC(=O)COC(=O)N1CCc2nc3ccccc3c(NCCO)c2C1] | 10-(2-Hydroxy-ethylamino)-3,4-dihydro-1H-benzo[b]-1,6-naphthyridine-2-carboxylic acid (5-chloro-2-methoxy-phenylcarbamoyl)methyl ester |
| 8 | 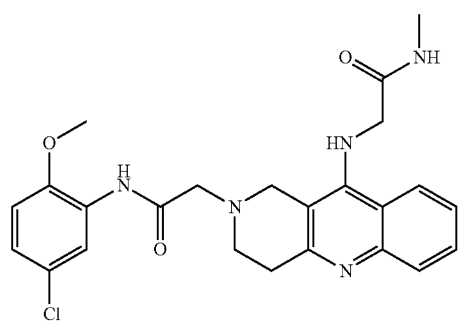 [SMILES: CNC(=O)CNc1c2c(nc3ccccc13)CCN(CC(=O)Nc1cc(Cl)ccc1OC)C2] | N-(5-Chloro-2-methoxyphenyl)-2-[10-(methylcarbamoyl-methylamino)-3,4-dihydro-1H-benzo[b]-1,6-naphthyridin-2-yl]-acetamide |
| 9 | 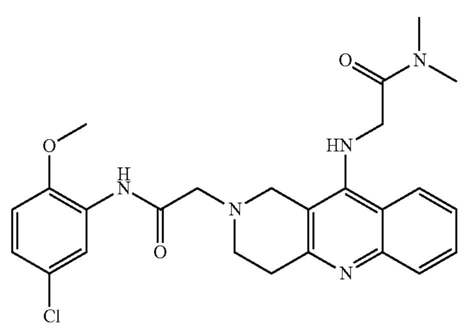 [SMILES: COc1ccc(Cl)cc1NC(=O)CN1CCc2nc3ccccc3c(NCC(=O)N(C)C)c2C1] | N-(5-Chloro-2-methoxyphenyl)-2-[10-(dimethylcarbamoyl-methylamino)-3,4-dihydro-1H-benzo[b]-1,6-naphthyridin-2-yl]-acetamide |

| Compound No. | Chemical Structure | Chemical Name |
|---|---|---|
| 10 | 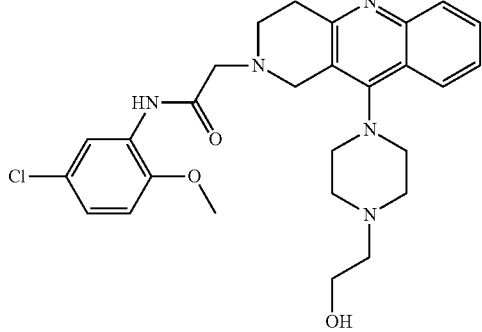 | N-(5-Chloro-2-methoxyphenyl)-2-[10-[4-(2-hydroxyethyl)-piperazin-1-yl]-3,4-dihydro-1H-benzo[b]-1,6-naphthyridin-2-yl]-acetamide |
| 11 | 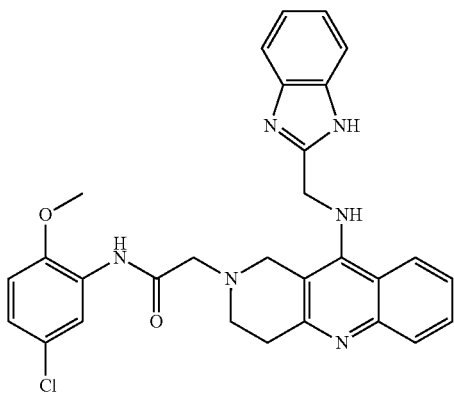 [SMILES: COc1ccc(Cl)cc1NC(=O)CN1CCc2nc3ccccc3c(NCc3nc4ccccc4[nH]3)c2C1] | 2-{10-[(1H-Benzimidazol-2-ylmethyl)amino]-3,4-dihydro-1H-benzo[b]-1,6-naphthyridin-2-yl]-N-(5-chloro-2-methoxy-phenyl)acetamide |
| 12 | 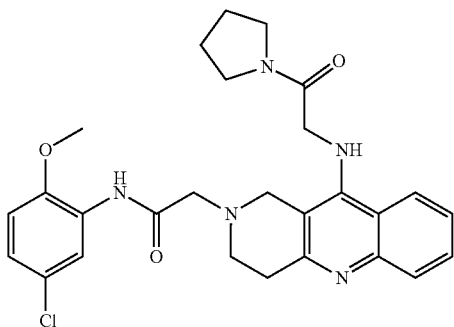 [SMILES: COc1ccc(Cl)cc1NC(=O)CN1CCc2nc3ccccc3c(NCC(=O)N3CCCC3)c2C1] | N-(5-Chloro-2-methoxyphenyl)-2-[10-(2-oxo-2-pyrrolidin-1-yl-ethylamino)-3,4-dihydro-1H-benzo[b]-1,6-naphthyridin-2-yl]-acetamide |
| 13 | 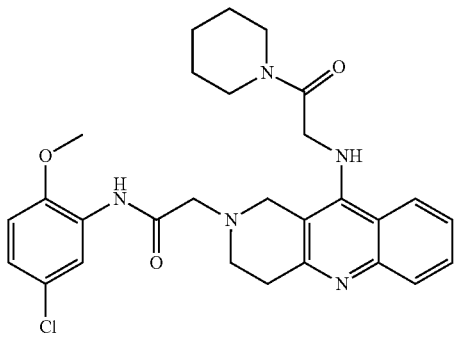 [SMILES: COc1ccc(Cl)cc1NC(=O)CN1CCc2nc3ccccc3c(NCC(=O)N3CCCCC3)c2C1] | N-(5-Chloro-2-methoxyphenyl)-2-[10-(2-oxo-2-piperidin-1-yl-ethylamino)-3,4-dihydro-1H-benzo[b]-1,6-naphthyridin-2-yl]-acetamide |

-continued

| Compound No. | Chemical Structure | Chemical Name |
|---|---|---|
| 14 | 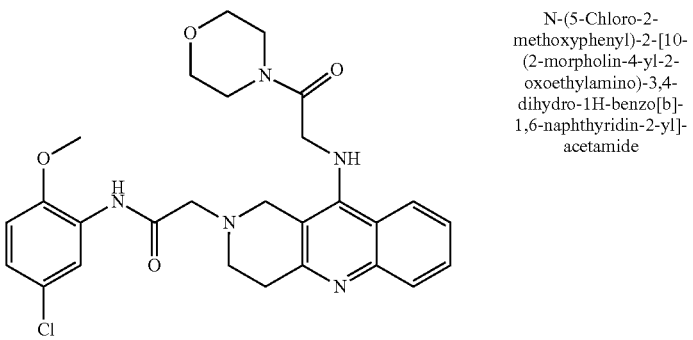 | N-(5-Chloro-2-methoxyphenyl)-2-[10-(2-morpholin-4-yl-2-oxoethylamino)-3,4-dihydro-1H-benzo[b]-1,6-naphthyridin-2-yl]-acetamide |
| 15 | 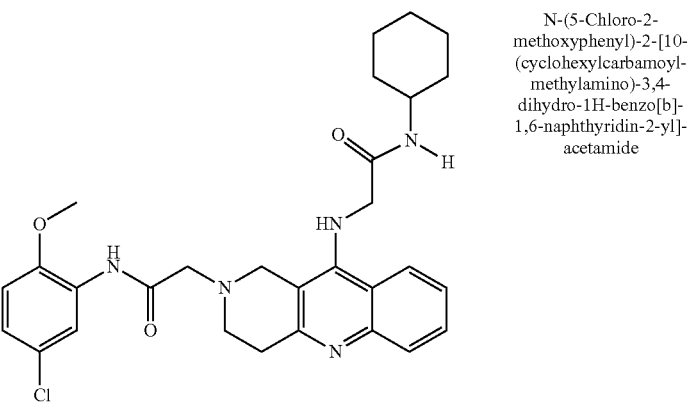 | N-(5-Chloro-2-methoxyphenyl)-2-[10-(cyclohexylcarbamoyl-methylamino)-3,4-dihydro-1H-benzo[b]-1,6-naphthyridin-2-yl]-acetamide |
| 16 | 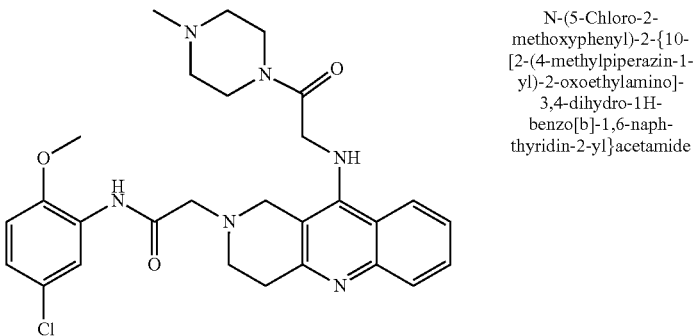 | N-(5-Chloro-2-methoxyphenyl)-2-{10-[2-(4-methylpiperazin-1-yl)-2-oxoethylamino]-3,4-dihydro-1H-benzo[b]-1,6-naphthyridin-2-yl}acetamide |
| 17 | 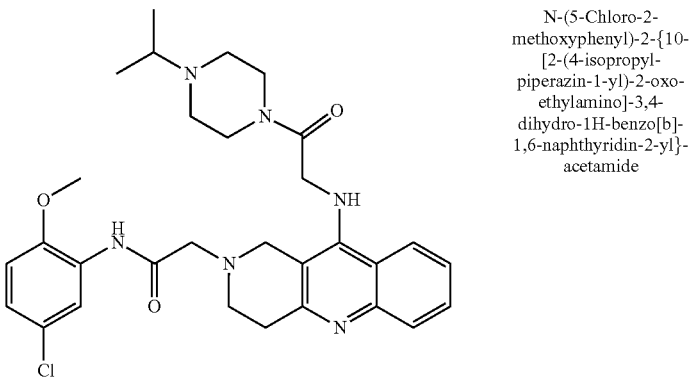 | N-(5-Chloro-2-methoxyphenyl)-2-{10-[2-(4-isopropyl-piperazin-1-yl)-2-oxo-ethylamino]-3,4-dihydro-1H-benzo[b]-1,6-naphthyridin-2-yl}-acetamide |

-continued

| Compound No. | Chemical Structure | Chemical Name |
|---|---|---|
| 18 | 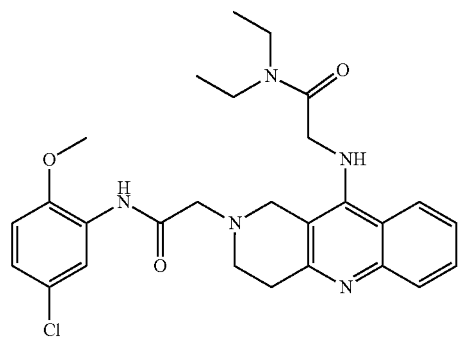 [SMILES: CCN(CC)C(=O)CNc1c2c(nc3ccccc13)CCN(CC(=O)Nc1cc(Cl)ccc1OC)C2] | N-(5-Chloro-2-methoxyphenyl)-2-[10-(diethylcarbamoyl-methylamino)-3,4-dihydro-1H-benzo[b]-1,6-naphthyridin-2-yl]-acetamide |
| 19 | 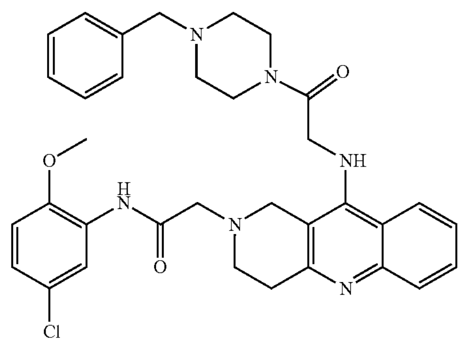 [SMILES: COc1ccc(Cl)cc1NC(=O)CN1CCc2nc3ccccc3c(NCC(=O)N3CCN(Cc4ccccc4)CC3)c2C1] | 2-{10-[2-(4-Benzyl-piperazin-1-yl)-2-oxo-ethylamino]-3,4-dihydro-1H-benzo[b]-1,6-naphthyridin-2-yl}-N-(5-chloro-2-methoxy-phenyl)acetamide |
| 20 | 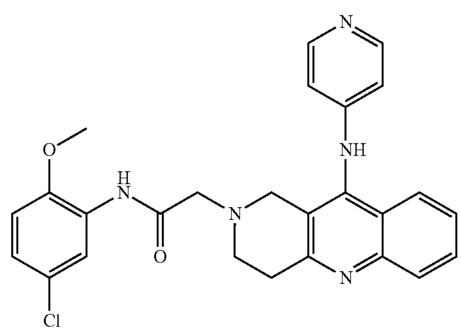 [SMILES: COc1ccc(Cl)cc1NC(=O)CN1CCc2nc3ccccc3c(Nc3ccncc3)c2C1] | N-(5-Chloro-2-methoxyphenyl)-2-[10-(pyridin-4-ylamino)-3,4-dihydro-1H-benzo[b]-1,6-naphthyridin-2-yl]-acetamide |
| 21 | 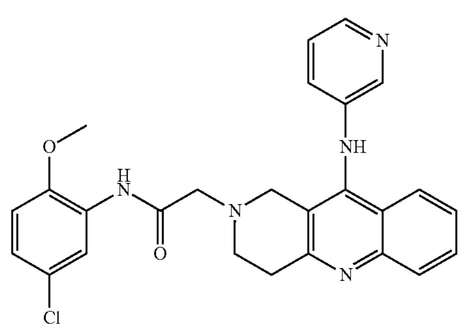 [SMILES: COc1ccc(Cl)cc1NC(=O)CN1CCc2nc3ccccc3c(Nc3cccnc3)c2C1] | N-(5-Chloro-2-methoxyphenyl)-2-[10-(pyridin-3-ylamino-3,4-dihydro-1H-benzo[b]-1,6-naphthyridin-2-yl]-acetamide |

-continued

| Compound No. | Chemical Structure | Chemical Name |
|---|---|---|
| 22 | 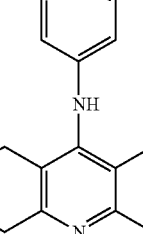 | N-(5-Chloro-2-methoxyphenyl)-2-(10-phenylamino-3,4-dihydro-1H-benzo[b]-1,6-naphthyridin-2-yl)-acetamide |
| 23 | 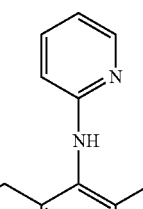 | N-(5-Chloro-2-methoxyphenyl)-2-[10-(pyridin-2-ylamino)-3,4-dihydro-1H-benzo[b]-1,6-naphthyridin-2-yl]-acetamide |
| 24 | 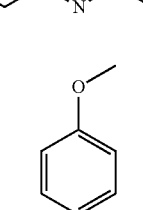 | N-(5-Chloro-2-methoxyphenyl)-2-[10-(4-methoxyphenyl-amino)-3,4-dihydro-1H-benzo[b]-1,6-naphthyridin-2-yl]acetamide | or pharmaceutically usable salts, solvates or stereoisomers thereof, including mixtures thereof in all ratios.

4. A process for preparation of compounds of the formula (I) according to claim 1 or pharmaceutically usable salts, solvates or stereoisomers thereof, comprising reacting a compound of formula (II)

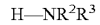

(II)

in which D, X, Y, R, $R^1$, $R^4$, $R^5$, m, n and p have the meanings indicated and L is a halogen, tosylate, mesylate or triflate,
with a compound of formula (III)

$$H\text{—}NR^2R^3 \qquad (III)$$

in which $R^2$, $R^3$ have the meanings indicated,
and/or converting a base or acid of the resultant compounds of the formula (I) into one of its salts,
or
reacting a compound of formula (IV)

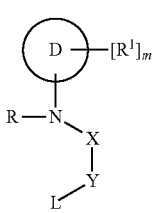

(IV)

in which D, X, Y, R, R¹ and m have the meanings indicated and L represents a halogen, tosylate, mesylate, triflate or a free or reactively modified OH group,
with a compound of formula (V)

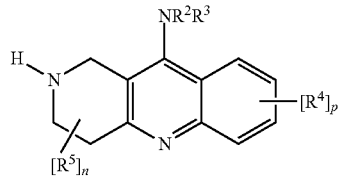

in which $R^2$, $R^3$, $R^4$, $R^5$, n and p have the meanings indicated,
and/or converting a base or acid of the resultant compounds of the formula (I) into one of its salts,
or
first reacting a compound of formula (VI)

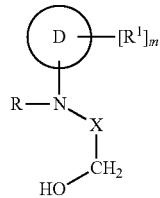

in which D, X, R, R¹ and m have the meanings indicated, with a carbonylation agent,
and then reacted with a compound of the formula (V)

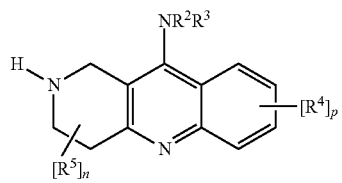

in which $R^2$, $R^3$, $R^4$, $R^5$, n and p have the meanings indicated,
and/or a base or acid of the resultant compounds of the formula (I) is converted into one of its salts.

5. A method of inhibiting an autotaxin comprising inhibiting said autotaxin with a compound according to claim 1.

6. A pharmaceutical composition comprising at least one compound of the formula (I) according to claim 1 and/or pharmaceutically usable salts, solvates or stereoisomers thereof, including mixtures thereof in all ratios, and optionally excipients and/or adjuvants.

7. A method for treating physiological and/or pathophysiological conditions in which inhibition, regulation and/or modulation of phosphodiesterase or lysophospholipase autotaxin plays a role, comprising administering an effective amount of a compound according to claim 1.

8. A method for treating glioblastomas, neuroblastomas, kidney cell carcinomas, prostate carcinomas, thyroid cancer, lung cancer, breast cancer, lymphomas or angiogenesis, mediated by autotaxin, said method comprising administering an effective amount of a compound according to claim according to claim 1.

9. A pharmaceutical composition according to claim 6, further comprising at least one additional pharmacologically active substance.

10. A method according to claim 7, wherein said compound is administered before and/or during and/or after the treatment with at least one additional pharmacologically active substance.

11. A kit comprising a therapeutically effective amount of at least one compound according to claim 1 and a therapeutically effective amount of at least one additional pharmacologically active substance which does not correspond to a compound according to claim 1.

\* \* \* \* \*

UNITED STATES PATENT AND TRADEMARK OFFICE
CERTIFICATE OF CORRECTION

| | | |
|---|---|---|
| PATENT NO. | : 9,029,387 B2 | |
| APPLICATION NO. | : 13/637161 | |
| DATED | : May 12, 2015 | |
| INVENTOR(S) | : Wolfgang Staehle et al. | |

It is certified that error appears in the above-identified patent and that said Letters Patent is hereby corrected as shown below:

IN THE CLAIMS

Column 60, Line 10, "Chemical Name" reads:

N-(5-Chloro-2-methoxyphenyl)-2-[10-[4-(2-hydroxyethyl)-piperazin-1-yl]-3,4-dihydro-1H-benzo[b]-1,6-naphthyridin-2-yl]-acetamide should read:

N-(5-Chloro-2-methoxyphenyl)-2-{10-[4-(2-hydroxyethyl)-piperazin-1-yl]-3,4-dihydro-1H-benzo[b]-1,6-naphthyridin-2-yl}-acetamide

Column 60, Line 11, "Chemical Name" reads:

2-{10-[(1H-Benzimidazol-2-ylmethyl)amino]-3,4-dihydro-1H-benzo[b]-1,6-naphthyridin-2-yl]-N-(5-chloro-2-methoxy-phenyl)acetamide should read:

2-{10-[(1H-Benzimidazol-2-ylmethyl)amino]-3,4-dihydro-1H-benzo[b]-1,6-naphthyridin-2-yl}-N-(5-chloro-2-methoxy-phenyl)acetamide Signed and Sealed this
Thirteenth Day of October, 2015

Michelle K. Lee
*Director of the United States Patent and Trademark Office*